United States Patent
Lyon et al.

(10) Patent No.: US 9,725,500 B2
(45) Date of Patent: Aug. 8, 2017

(54) METHODS FOR SCREENING ANTIBODIES

(75) Inventors: Robert Lyon, Sammamish, WA (US); Dennis Benjamin, Redmond, WA (US); Maureen Ryan, Bellevue, WA (US)

(73) Assignee: Seattle Genetics, Inc., Bothell, WA (US)

( * ) Notice: Subject to any disclaimer, the term of this patent is extended or adjusted under 35 U.S.C. 154(b) by 481 days.

(21) Appl. No.: 13/581,236

(22) PCT Filed: Feb. 28, 2011

(86) PCT No.: PCT/US2011/026534
§ 371 (c)(1),
(2), (4) Date: Aug. 24, 2012

(87) PCT Pub. No.: WO2011/109308
PCT Pub. Date: Sep. 9, 2011

(65) Prior Publication Data
US 2012/0322686 A1    Dec. 20, 2012

Related U.S. Application Data

(60) Provisional application No. 61/309,725, filed on Mar. 2, 2010, provisional application No. 61/323,433, filed on Apr. 13, 2010.

(51) Int. Cl.
| | |
|---|---|
| *A61K 38/00* | (2006.01) |
| *A61K 39/00* | (2006.01) |
| *C07K 16/00* | (2006.01) |
| *A61K 47/48* | (2006.01) |

(52) U.S. Cl.
CPC ........ *C07K 16/00* (2013.01); *A61K 47/48384* (2013.01); *C07K 2317/24* (2013.01)

(58) Field of Classification Search
CPC .................. C07K 16/00; A61K 47/48384
See application file for complete search history.

(56) References Cited

U.S. PATENT DOCUMENTS

| | | | |
|---|---|---|---|
| 2002/0197694 | A1 | 12/2002 | Shao |
| 2004/0038331 | A1 | 2/2004 | Reddy et al. |
| 2005/0276812 | A1 | 12/2005 | Ebens, Jr. et al. |
| 2007/0160617 | A1 | 7/2007 | Ma et al. |
| 2008/0233660 | A1 | 9/2008 | Uhlen et al. |
| 2009/0047296 | A1 | 2/2009 | Doronina et al. |
| 2009/0136526 | A1 | 5/2009 | McDonagh et al. |
| 2009/0226465 | A1 | 9/2009 | Jackson |
| 2009/0280056 | A1 | 11/2009 | Dennis et al. |
| 2010/0021474 | A1 | 1/2010 | Kirchhofer et al. |
| 2010/0034837 | A1 | 2/2010 | Beria et al. |

(Continued)

FOREIGN PATENT DOCUMENTS

| | | |
|---|---|---|
| CA | 1283852 | 5/1991 |
| WO | 2005084390 | 9/2005 |

OTHER PUBLICATIONS

Carter et al., "Antibody-Drug Conjugates for Cancer Therapy," The Cancer Journal 14(3)154-169, May/Jun. 2008.

(Continued)

*Primary Examiner* — Cherie M Stanfield
(74) *Attorney, Agent, or Firm* — Seattle Genetics, Inc.

(57) ABSTRACT

The invention provides methods for making antibody conjugates for use in antibody screening assays and antibody conjugates produced by the claimed methods.

23 Claims, 11 Drawing Sheets

(56) References Cited

U.S. PATENT DOCUMENTS

2011/0009287 A1    1/2011   Gao

OTHER PUBLICATIONS

Lyon et al., "Development of parallel conjugation and assay methodologies to screen for antibodies with optimal properties for use as antibody-drug conjugates," AACR 101st Annual Meeting, Apr. 17-21, 2010.
Klussman, et al., "Secondary mAb-vcMMAE Conjugates Are Highly Sensitive Reporters of Antibody Internalization via the Lysosome Pathway," Bioconjugate Chem. 15:765-773, 2004.
Lyon et al., "Conjugation of Anticancer Drugs Through Endogenous Monoclonal Antibody Cysteine Residues," Methods in Enzymology 502, pp. 123-138, 2012.

METHODS FOR SCREENING ANTIBODIES

This application is the national stage filing under 35 U.S.C. §371 of International Application No. PCT/US2011/026534 filed Feb. 28, 2011 and published Sep. 9, 2011 as International Publication No. WO 2011/109308, which in turn claims the benefit of U.S. Provisional Application No. 61/309,725 filed Mar. 2, 2010 and U.S. Provisional Application No. 61/323,433 filed Apr. 13, 2010; each of which is incorporated by reference herein in their entireties.

BACKGROUND OF THE INVENTION

The activity of antibody-drug conjugates (ADCs) on cancer cells can be affected by a multitude of factors, such as binding affinity, rate of internalization, subcellular trafficking, and efficient drug release within the target cell population. Consequently, the properties of an ideal antibody for drug delivery are not necessarily the same as those for a therapeutic unconjugated antibody. Furthermore, indirect assays involving the use of secondary antibodies to screen for optimal ADCs can be misleading, since cross-linking on the cell surface can lead to altered downstream events, and the affinity of the secondary antibody constrains the dynamic range of the assay. When seeking candidate antibodies directed against a novel antigen for ADC therapy, it is therefore most desirable to screen a large antibody panel in the form of ADCs and evaluate their cytotoxic activities, since these results provide a direct measurement of parameters that can affect cytotoxic activity. However, when dealing with microgram quantities of a large number of antibodies as is typical of an antibody discovery campaign, the yields from conventional conjugation methodologies are limiting. A need exists for improved methods of screening antibodies for use as ADCs. This present invention addresses this and other needs.

SUMMARY OF THE INVENTION

The invention provides methods for making antibody conjugates for use in antibody screening assays and antibody conjugates produced by the claimed methods.

In some embodiments, the methods comprise the steps of providing a first and second antibody-containing sample wherein the first and second antibody-containing sample vary with respect to antibody quantity and antibody sequence provided that substantially all of the antibody present in the first sample is of the same sequence and substantially all of the antibody present in the second sample is of the same sequence; immobilizing the antibodies on a solid support to provide a first and second sample comprising immobilized antibodies; fully reducing the reducible disulfide bonds of the immobilized antibodies to provide a first sample comprising reduced immobilized antibodies and second sample comprising reduced immobilized antibodies, wherein the reduction is selective for the reducible disulfide bonds; reacting the reduced immobilized antibodies with capping agent, drug or drug-linker, and optionally a detection agent to provide immobilized antibody conjugates, wherein the capping agent, drug or drug-linker, and optional detection agent selectively react with reactive thiols, the capping agent, drug or drug-linker, and optional detection agent are provided in molar excess, and the ratio of capping agent, drug or drug linker, and optional detection agent is selected so as to achieve a desired level of drug loading; and eluting the antibody conjugates to provide a first sample of free antibody conjugates and second sample of free antibody conjugates.

In some embodiments, the methods comprise the steps of providing a plurality of samples of unpurified hybridoma supernatant comprising unquantified antibody produced from a plurality of hybridoma clones, wherein the plurality of samples vary with respect to antibody quantity and antibody sequence provided that, in a majority of the plurality of the samples, substantially all of the antibody present in each sample is from a single hybridoma clone; immobilizing the unquantified antibodies on a solid support to provide a plurality of samples comprising immobilized antibodies; fully reducing the interchain disulfides of the immobilized antibodies to provide a plurality of samples comprising reduced immobilized antibodies; reacting the reduced immobilized antibodies with capping agent, drug or drug-linker, and a detection agent to provide immobilized antibody conjugates, wherein the capping agent, drug or drug-linker, and detection agent selectively react with reactive thiols, the capping agent, drug or drug-linker, and optional detection agent are provided in molar excess, and the ratio of capping agent, drug or drug linker and detection agent is selected so as to achieve a desired level of drug loading; and eluting the antibody conjugates from the solid supports to provide a plurality of antibody conjugate compositions.

In some embodiments, the methods comprise the steps of providing a plurality of antibody containing samples that vary with respect to antibody quantity and antibody sequence provided that, in a majority of the plurality of the antibody-containing samples, substantially all of the antibody present in a single sample is of the same sequence; immobilizing the antibodies on a solid support to provide a plurality of samples comprising immobilized antibodies; fully reducing the reducible disulfide bonds of the immobilized antibodies to provide a plurality of samples comprising reduced immobilized antibodies, wherein the reduction is selective for reducible disulfide bonds; reacting the reduced immobilized antibodies with capping agent, drug or drug-linker, and optionally a detection agent to provide a plurality of samples comprising immobilized antibody conjugates, wherein the capping agent, drug or drug-linker, and optional detection agent selectively react with reactive thiols, the capping agent, drug or drug-linker, and optional detection agent are provided in molar excess, and the ratio of capping agent, drug or drug linker; and optional detection agent is selected so as to achieve a desired level of drug loading; and eluting the antibody conjugates to provide a plurality of antibody conjugate compositions comprising free antibody conjugates.

In some embodiments, the methods comprise the steps of providing a plurality of antibody containing samples that vary with respect to antibody quantity and antibody sequence provided that, in a majority of the plurality of the antibody containing samples, substantially all of the antibody present in a single sample is of the same sequence; immobilizing the antibodies on a solid support to provide a plurality of samples comprising immobilized antibodies; fully reducing the reducible disulfide bonds of the immobilized antibodies to provide a plurality of samples comprising reduced immobilized antibodies, wherein the reduction is selective for reducible disulfide bonds; reacting the reduced immobilized antibodies with capping agent, and a detection agent to provide a plurality of samples comprising immobilized antibody conjugates, wherein the capping and detection agent selectively react with reactive thiols, the capping agent, and detection agent are provided in molar excess, and the ratio of capping agent and detection agent is selected so as to achieve a desired level of detection agent and/or capping agent loading; and eluting the antibody conjugates to provide a plurality of antibody conjugate compositions comprising free antibody conjugates.

In some embodiments, the methods comprise the steps of providing a plurality of antibody containing samples that vary with respect to antibody quantity and antibody sequence provided that, in a majority of the plurality of the antibody-containing samples, substantially all of the antibody present in a single sample is of the same sequence; immobilizing the antibodies on a solid support to provide a plurality of samples comprising immobilized antibodies; fully reducing the reducible disulfide bonds of the immobilized antibodies to provide a plurality of samples comprising reduced immobilized antibodies, wherein the reduction is selective for reducible disulfide bonds; reacting the reduced immobilized antibodies with capping agent, drug or drug-linker, and optionally a detection agent to provide a plurality of samples comprising immobilized antibody conjugates, wherein the capping agent, drug or drug-linker, and optional detection agent selectively react with reactive thiols, the capping agent, drug or drug-linker, and optional detection agent are provided in molar excess, and the ratio of capping agent, drug or drug linker, and optional detection agent is selected so as to achieve a desired level of drug loading; eluting the antibody conjugates to provide a plurality of antibody conjugate compositions comprising free antibody conjugates; assaying for an activity of the antibody conjugates; and selecting an antibody of the basis of the outcome of the assay.

In some embodiments, the methods comprise the steps of providing a plurality of antibody containing samples that vary with respect to antibody quantity and antibody sequence provided that, in a majority of the plurality of the antibody containing samples, substantially all of the antibody present in a single sample is of the same sequence; immobilizing the antibodies on a solid support to provide a plurality of samples comprising immobilized antibodies; fully reducing the reducible disulfide bonds of the immobilized antibodies to provide a plurality of samples comprising reduced immobilized antibodies, wherein the reduction is selective for reducible disulfide bonds; reacting the reduced immobilized antibodies with capping agent, and a detection agent to provide a plurality of samples comprising immobilized antibody conjugates, wherein the capping agent and detection agent selectively react with reactive thiols, the capping agent, and detection agent are provided in molar excess, and the ratio of capping agent and detection agent is selected so as to achieve a desired level of detection agent and/or capping agent loading; eluting the antibody conjugates to provide a plurality of antibody conjugate compositions comprising free antibody conjugates; assaying for an activity of the antibody conjugates; and selecting an antibody of the basis of the outcome of the assay.

These and other aspects of the present invention may be more fully understood by reference to the following detailed description, non-limiting examples of specific embodiments, and the appended figures.

DETAILED DESCRIPTION OF THE INVENTION

Definitions

Figure 1:
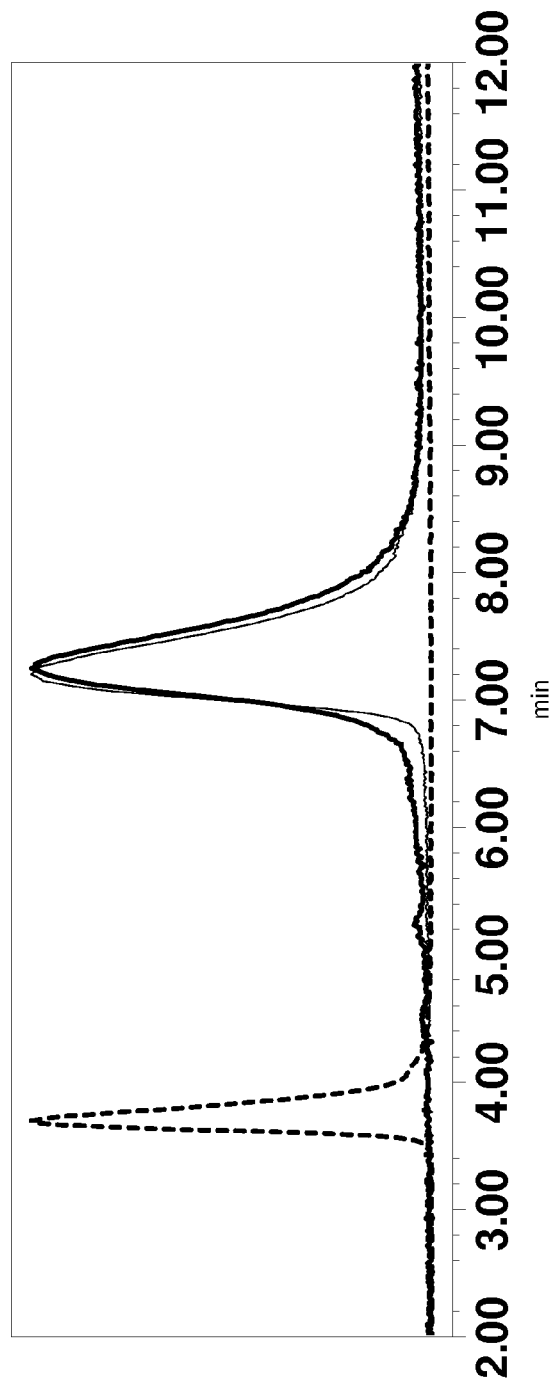
FIG. 1. This figure provides an overlay of hydrophobic interaction chromatograms of a murine IgG1 in its unconjugated form (dashed), fully reduced and conjugated with mcMMAF in solution (heavy solid line), and fully reduced and conjugated with mcMMAF while immobilized on Protein G sepharose (light solid line).

The term "antibody" as used herein refers to (a) immunoglobulin polypeptides and immunologically active portions of immunoglobulin polypeptides, i.e., polypeptides of the immunoglobulin family, or fragments thereof or (b) conservatively substituted derivatives of such immunoglobulin polypeptides or fragments that immunospecifically bind to a target antigen. The antibodies (including antibody fragments) for use in the present invention contain (i) an antigen binding site that immunospecifically binds to a target antigen, (ii) at least one reducible disulfide bond (e.g., interchain disulfide bond) and (iii) a domain capable of reversibly binding to a solid phase. In some embodiments, an antibody will comprise a full length Fc region and binding to the solid phase will be through the Fc region. In some embodiments, an antibody will comprise one or more Fc domains of an antibody and binding to the solid phase will be through the one or more Fc domains. In some embodiments, the domain capable of reversibly binding to a solid phase will not be a Fc region, but will be a domain engineered on the antibody, such as, for example, an affinity tag. The term antibody includes antibodies that are non-fucosylated or have reduced core fucosylation. Antibodies are generally described in, for example, Harlow & Lane, Antibodies: *A Laboratory Manual* (Cold Spring Harbor Laboratory Press, 1988). The basic unit of an intact antibody structure is a complex of four polypeptides—two identical low molecular weight ("light") chains and two identical high molecular weight ("heavy") chains, linked together by both non-covalent associations and by disulfide bonds. The class and subclass of an antibody is its isotype. Antibodies can be, for example, in their natural tetrameric form (2 light chains and 2 heavy chains) and can be of any of the known isotypes IgG, IgA, IgM, IgD and IgE and their subtypes, for example, human IgG1, IgG2, IgG3, IgG4 and mouse IgG1, IgG2a, IgG2b, and IgG3. The antibodies are preferably monoclonal.

In the context of an antibody, the term "reducible disulfide bond" refers to a disulfide bond that is (i) reducible while the antibody is reversibly bound to a solid support, and (ii) reducible under mild reducing conditions. Mild reducing conditions are those conditions that generally do not cause any substantial denaturation of the antibody and generally do not affect the antigen binding affinity of the antibody. An example of mild reducing conditions is reduction under aqueous conditions at near neutral pH with a weak reducing agent. An example of weak reducing agents are TCEP (tris(2-carboxyethyl)phosphine) and DTT (dithiothreitol). Accordingly, one example of mild reducing conditions is reduction in an excess of TCEP or DTT at a temperature of about 5° C. to about 37° C. and a pH of from about 5 to 8. Because organic cosolvents can substantially denature proteins, if organic cosolvents are to be used in the denaturation and/or subsequent conjugation steps, it should be a minimal amount of cosolvents (e.g., less than 20%, preferably less than 15%, 10%, or even 5%) such that substantial denaturation of the antibody does not occur. Typically, the reducible disulfide bonds are those that are solvent accessible, i.e., not buried within the folded domains of the antibody. (The skilled artisan will understand that when reducing the reducible disulfide bonds of a population of antibodies within a sample according to the methods described herein, there may be a minor amount of antibodies that do become irreversibly denatured (e.g., generally less than 10%, even less than 5% or 3%)). Typically, in an antibody, a disulfide bond is present as a result of the oxidation of the thiol (—SH) side groups of two cysteine residues. These residues may lie on different polypeptide chains (interchain), or on the same polypeptide chain (intrachain). As a result of the oxidation, a disulfide bond (——S——S——) is formed between the beta carbons of the original cysteine residues. Treatment of the disulfide bond with a reducing agent causes reductive cleavage of the disulfide bonds to generate two free thiol groups, i.e., reactive thiols. In some embodiments, the reducible disulfide bond is naturally occurring. In some aspects, the term "reducible disulfide bond" refers to the naturally occurring interchain disulfide bonds of an antibody. In some embodiments, a sulfhydryl group(s) is chemically introduced into the antibody. Suitable methods for introducing sulfhydryl groups include recombinant DNA technology. Sulfhydryl groups can be introduced into an antibody, for example, within the antibody or at the carboxy-terminus. Because it is preferable that the methods described herein do not interfere with the antigen binding activity of the resultant antibody conjugates, it is preferable that introduced sulfhydryl groups be introduced at a site other than the antigen binding site of the antibody. Preferably introduced sulfhydryl groups are introduced at a site other than the heavy or light chain variable regions, e.g., preferably in the constant region of an antibody. In some embodiments, a cysteine residue is engineered into an antibody. The sulfhydryl group of the cysteine will typically form a disulfide bond that can then be reduced using the methods described herein.

In the context of a fusion protein, the term "reducible disulfide bond" refers to a disufide bond of a fusion protein that is (i) reducible while the fusion protein is reversibly bound to a solid support, and (ii) reducible under mild reducing conditions. For a fusion protein to be of use in the present methods, it should remain generally intact following reduction of the reducible disulfide bond(s). An example of mild reducing conditions is reduction under aqueous conditions at near neutral pH with a weak reducing agent. In some preferred embodiments, the reducible disulfide bond will be in the Ig domain of the fusion protein. In some embodiments, the disulfide bond is naturally occurring and refers to the naturally occurring interchain disulfide bonds of the Ig domain of the fusion protein. In some embodiments, a sulfhydryl group(s) is chemically introduced into Ig domain of the fusion protein.

The term "monoclonal antibody" refers to an antibody that is derived from a single cell clone, including any eukaryotic or prokaryotic cell clone, or a phage clone, and not the method by which it is produced. Thus, the term "monoclonal antibody" is not limited to antibodies produced through hybridoma technology.

The term "Fc region" refers to a constant region of an antibody, e.g., a $C_H1$-hinge-$C_H2$-$C_H3$ domain, optionally having a $C_H4$ domain, or a conservatively substituted derivative of such an Fc region.

The term "Fc domain" refers to the constant region domain of an antibody, e.g., a $C_H1$, hinge, $C_H2$, $C_H3$ or $C_H4$ domain, or a conservatively substituted derivative of such an Fc domain.

An "antigen" is a molecule to which an antibody specifically binds.

A "cytotoxic agent" refers to an agent that has a cytotoxic and/or cytostatic effect on a cell. A "cytotoxic effect" refers to the depletion, elimination and/or the killing of a target cell(s). A "cytostatic effect" refers to the inhibition of cell proliferation.

The term "interchain disulfide bond," in the context of an antibody, refers to a disulfide bond between two heavy chains, or a heavy and a light chain of an antibody.

As used herein, "free antibody conjugates" refers to antibody conjugates that are not immobilized on a solid support, e.g., antibodies that have been released from a solid support.

The abbreviation "AFP" refers to dimethylvaline-valine-dolaisoleuine-dolaproine-phenylalanine-p-phenylenediamine having the general formula shown immediately following:

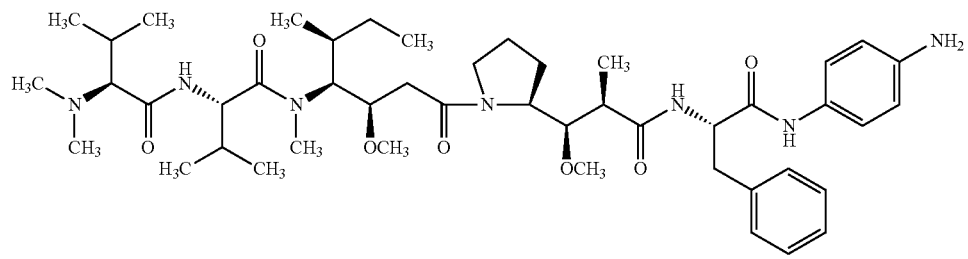

The abbreviation "MMAE" refers to monomethyl auristatin E having the general formula shown immediately following:

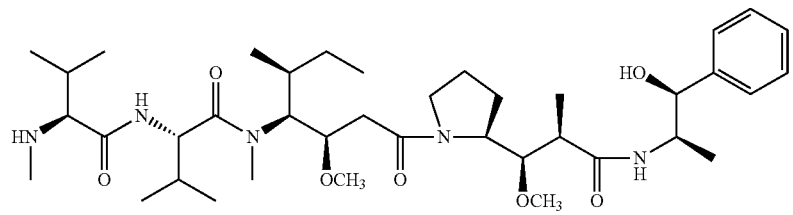

The abbreviation "MMAF" refers to dovaline-valine-dolaisoleunine-dolaproine-phenylalanine having the general formula shown immediately following:

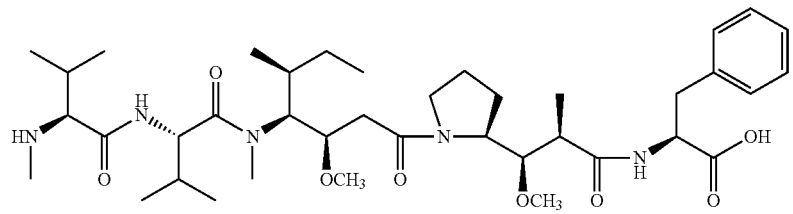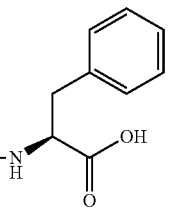

The abbreviation "AEB" refers to an ester produced by reacting auristatin E with paraacetyl benzoic acid. The abbreviation "AEVB" refers to an ester produced by reacting auristatin E with benzoylvaleric acid.

The phrase "pharmaceutically acceptable salt," as used herein, refers to pharmaceutically acceptable organic or inorganic salts of a molecule or macromolecule. Acid addition salts can be formed with amino groups. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1' methylene bis-(2-hydroxy 3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

General

A method of directly screening antibodies on the basis of their performance as ADCs or as unconjugated antibodies (i.e., naked antibodies) has been invented. A labeling technique has been developed that is insensitive to the concentration of antibody present in a sample and applicable to small amounts of antibody allowing for a comparison of the activities of individual antibodies of a heterogenous population of antibodies.

The screening assay is useful for identifying antibodies with desired characteristics. The antibodies can be generated though any technique known in the art for generating antibodies provided that the antibodies to be screened comprise (i) an antigen binding site that immunospecifically binds to a specific antigen, (ii) at least one reducible disulfide bond (e.g., interchain disulfide bond) and (iii) a domain capable of binding to a solid phase.

In one aspect of the invention, a plurality of antibody-containing samples are provided. The phrase "a plurality of samples" refers to two or more samples. Because the methods provided herein are ideally suited for high throughput screening, in one aspect of the invention, the methods are performed simultaneously on at least tens or at least hundreds of samples. One of the strengths of the methods provided herein is that a comparison between antibodies can be made even though the antibody-containing samples may not contain the same quantity of antibody. Accordingly, in one aspect, the samples vary with respect to antibody quantity and with respect to antibody sequence. For example, in one aspect, a first sample will comprise a first antibody at a first quantity and a second sample will comprise a second antibody at a second quantity. The first and second quantities will vary and the first and second antibodies will vary. In embodiments wherein it is desirable to compare antibodies that target the same antigen, the antibodies will immunospecifically bind to the same antigen. For purpose of clarification, the phrase "wherein the plurality of samples vary with respect to antibody quantity and antibody sequence" does not require that all of the samples within a plurality of samples vary with respect to antibody quantity and antibody sequence, only that there is certain level of heterogeneity between samples. Although there is a variance in antibody sequence (e.g., a first sample will contain a different antibody than a second sample), it is preferable that a single sample contain one antibody, i.e., that the antibody present in a single sample is of the same sequence. The phrase "substantially all of the antibody present in a single sample is of the same sequence" reflects the preference that a single sample contain one antibody with the recognition that, in some samples, there may be some contamination with another antibody. Preferably, in those samples that have some contamination with another antibody, there is less than 30%, preferably less than 20%, preferably less than 15%, more preferably less than 10%, and even more preferably less than 5%, less than 4%, or less than 3% of contamination with another antibody. In preferred embodiments, the majority of antibody-containing samples (greater that 50% of samples and even more preferably greater than 60%, greater than 70%, greater than 75%, or even greater than 80% of the samples) in a plurality of antibody-containing samples contain one antibody with no or minor amounts of contamination with another antibody (e.g., less than 15%, preferably even less than 10% or less than 5% contamination with another antibody). In some preferred embodiments, a majority of the antibody-containing samples will comprise antibodies that immunospecifically bind to the same antigen.

The antibodies to be screened using the present methods can be targeted to any antigen. In exemplary embodiments, an antibody to be screened by the present methods will immunospecifically bind to an antigen selected from CD19, CD20, CD21, CD22, CD30, CD33, CD38, CD40, CD70, CD74, CD83, CD133, CD138, CD200, or CD276. In other embodiments, the antibody will immunospecifically bind to BMPR1B, LAT1 (SLC7A5), STEAP1, MUC16, MUC1, megakaryocyte potentiating factor (MPF), Napi3b, Sema 5b, PSCA hlg, ETBR (Endothelin type B receptor), STEAP2, TrpM4, CRIPTO, CD21, CD79a, CD79b, FcRH2, HER2, HER3, HER4, NCA, MDP, IL20Rα, Brevican, Ephb2R, ASLG659, PSCA, PSMA, TMPRSS2, TMPRSS4, GEDA, BAFF-R, CXCRS, HLA-DOB, P2X5, CD72, LY64, FCRH1, VEGF, PLAC1, VEGFR1 VEGFR2, or IRTA2. In other embodiments, the antibody will immunospecifically bind to CD2, CD3, CD3E, CD4, CD11, CD11a, CD14, CD16, CD18, CD19, CD23, CD25, CD28, CD29, CD30, CD32, CD40L, CD51, CD52, CD54, CD56, CD70, CD80, CD123, CD133, CD138, CD147, CD227, or CD276. In other embodiments, the antibody will immunospecifically bind to IL-1, IL-1R, IL-2, IL-2R, IL-4, IL-5, IL-6, IL-6R, IL-8, IL-12, IL-15, IL-18, or IL-23. In other embodiments, the antibody will immunospecifically bind to a protein from the solute carrier family of proteins (e.g., solute carrier family 44, member 4 (protein encoded by SLC44A4 gene) or solute carrier family 34, member 2 (protein encoded by the SLC34A2 gene)); LIV-1 (protein encoded by SLC39A6 gene); protein from the SLAM family of proteins (e.g., SLAM family members 1, 2, 3, 4, 5, 6, 7, 8 or 9); protein from the mucin family of proteins (e.g., MUC1, MUC2, MUC3, MUC4, MUC5, MUC6, MUC7, MUCK, MUC9, MUC10, MUC11, MUC12, MUC13, MUC14, MUC15, or MUC16); protein from the STEAP family of proteins (e.g., STEAP1, STEAP2, STEAP3 or STEAP4); a protein from the tumor necrosis factor receptor family (e.g., TNF-RI, TNF-RII, DR1, DR2, DR3, DR4, DR5); MN protein; mesothelin protein; protein encoded by the Slitrk family of proteins (e.g., SLITRK1, SLITRK2, SLITRK3, SLITRK4, SLITRK5, or SLITRK6), or a protein encoded by the GPNMB gene.

The antibody-containing samples can be generated in many different ways. There are many techniques known in the art for generating antibodies. For example, antibodies that are useful in the present methods can be produced by recombinant expression techniques, phage display technique, from hybridomas, from myelomas, from other antibody expressing mammalian cells, and from combinations thereof. Antibodies to be used in the present invention can be of any species (e.g., human, murine, rat) and can be of mixed species, e.g., chimeric. Antibodies to be used in the present invention can comprise full length variable regions or fragments thereof.

A variety of mammalian cells and cell lines can be utilized to express an antibody. For example, mammalian cells such as Chinese hamster ovary cells (CHO) (e.g., DG44, Dxb11, CHO-K, CHO-K1 and CHO-S) can be used. In some embodiments, human cell lines are used. Suitable myeloma cell lines include SP2/0 and IR983F and human myeloma cell lines such as Namalwa. Other suitable cells include human embryonic kidney cells (e.g., HEK293), monkey kidney cells (e.g., COS), human epithelial cells (e.g., HeLa), PERC6, Wil-2, Jurkat, Vero, Molt-4, BHK, and K6H6. Other suitable host cells include YB2/0 cells.

Any antibody generating techniques can be used to generate the antibody-containing samples described herein provided that the antibodies generated can be immobilized on a solid support and contain at least one reducible disulfide bond. In some embodiments, the antibody will be generated by a method known in the art and will be modified in order to place it in condition for use in the present methods. For example, antibodies generated by phage display or other methods can be modified to contain an affinity tag and/or can be reformatted to express a Fc region. For an overview of phage display technology for producing antibodies, see Schmitz et al., 2000, *Placenta* 21, supplement A, S106-112. See also Lightwood et al., 2006, *Journal of Immunological Methods* 316, 133-143.

In some aspects, the antibodies to be assayed are generated using well known hybridoma techniques. For example, in some embodiments, the host cells are from a hybridoma. Hybridoma techniques are generally discussed in, for example, Harlow et al., *Antibodies: A Laboratory Manual* (Cold Spring Harbor Laboratory Press, 2nd ed., 1988); and Hammerling, et al., In *Monoclonal Antibodies and T-Cell Hybridomas*, pp. 563-681 (Elsevier, N.Y., 1981). Antibodies can also be generated using immortal or conditionally immortal cell lines other than hybridoma cell lines, including, for example, antibodies generated from conditionally immortal cell lines from H-2K$^b$-tsA58 mice (Pasqualinie and Arap, *PNAS,* 2004, 101(1), 257-259). These technologies can be used to generate fully rodent, chimeric rodent-human, or human antibodies. For example, for an overview of a technology for producing human antibodies from immunized transgenic mice using hybridoma technology, see Lonberg and Huszar, 1995, *Int. Rev. Immunol.* 13:65-93.

In addition, companies such as Amgen, Inc. (Thousand Oaks, Calif.) and BMS (Princeton, N.J.) can be engaged to provide human antibodies directed against a selected antigen using technology similar to that referenced above. Completely human antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a target polypeptide. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93).

The present methods do not require a purification step prior to antibody immobilization on a solid support. In some aspects, the antibody provided in the antibody-containing sample is not purified. In some embodiments, unpurified cell culture supernatant or unpurified conditioned media is provided as the antibody-containing sample. For example, in some embodiments wherein hybridoma technology is used to generate antibodies, the antibody-containing samples are unpurified hybridoma supernatant samples. In some aspects, the supernatant samples vary with respect to antibody quantity and antibody sequence. It is preferable that a single hybridoma supernatant sample contain antibody from a single hybridoma clone, although antibody-containing samples can contain contamination with other antibodies. Methods of picking clonal populations from hybridomas are known in the art as are methods of generating hybridoma supernatant. For example, in one aspect, newly fused hybridomas are plated in semi-solid media (e.g., methylcellulose) with a selective medium (e.g., a medium that promotes the survival and proliferation of hybridoma cells and the elimination of non-fused B cells and myeloma cells. Examples of such a medium include one containing hypoxanthine, aminopterin and thymidine). Clonal IgG-producing colonies are selected and placed in invididual wells containing media to support cell line expansion and antibody production. The resulting hybridoma supernatant can be assayed by the present methods. In another aspect, hybridoma cells are cloned using a limited dilution approach. In some embodiments, prior to immobilization and conjugation, the unpurified hybridoma culture supernatants are screened for the presence of antibodies with desired antigen specificity. In some embodiments, from about 1 ml to about 5 mls of hybridoma supernatant is provided.

In some embodiments, the unpurified cell culture supernatant is other than hybridoma supernatant, e.g., CHO cell culture supernatant (e.g., DG44, Dxb 11, CHO-K1 and CHO-S cell lines), or other cell culture supernatant.

In some embodiments, the antibody in the antibody-containing samples is produced in culture media lacking endogenous IgG, and, in particular, culture media lacking bovine IgG. In some embodiments, the culture medium is depleted of endogenous IgG prior to use (see, for example, example 8). Suitable culture media include those containing, for example, salts, carbon source (e.g., sugars), nitrogen source, amino acids, trace elements, antibiotics, selection agents, and the like, as required for growth. Commerically available media as well as commercially available cloning media, including IgG depleted cloning media can be used. The culture conditions, such as temperature, pH, and the like, will be apparent to the ordinarily skilled artisan.

The present methods use a solid support for conjugation of the antibodies to a desired chemical entity. Because the present methods are performed in solid phase and not in solution, the present methods can be performed with samples that contain very small amounts (e.g., 1 to 500 µg) of antibody. In some embodiments, there will be from 1 µg to 100 µg, from 1 µg to 50 µg, from 1 µg to 20 µg, from 3 µg to 100 µg, from 3 µg to 50 µg, from 3 µg to 20, from 5 µg to 100 µg, from 5 µg to 50 µg, from 5 µg to 20 µg of antibody present in a single sample. In one aspect, at least one of the samples in a plurality of samples will have from 1 µg to 100 µg, from 1 µg to 50 µg, from 1 µg to 20 µg, from 3 µg to 100 µg, from 3 µg to 50 µg, from 3 µg to 20, from 5 µg to 100 µg, from 5 µg to 50 µg, from 5 µg to 20 µg of antibody present.

A solid support refers to an insoluble, functionalized material to which the antibodies can be reversibly attached, either directly or indirectly, allowing them to be separated from unwanted materials, for example, excess reagents, contaminants, and solvents. Examples of solid supports include, for example, functionalized polymeric materials, e.g., agarose, or its bead form Sepharose®, dextran, polystyrene and polypropylene, or mixtures thereof; compact discs comprising microfluidic channel structures; protein array chips; pipet tips; membranes, e.g., nitrocellulose or PVDF membranes; and microparticles, e.g., paramagnetic or non-paramagnetic beads. In some embodiments, an affinity medium will be bound to the solid support and the antibody will be indirectly attached to solid support via the affinity medium. In one aspect, the solid support comprises a protein A affinity medium or protein G affinity medium. A "protein A affinity medium" and a "protein G affinity medium" each refer to a solid phase onto which is bound a natural or synthetic protein comprising an Fc-binding domain of protein A or protein G, respectively, or a mutated variant or fragment of an Fc-binding domain of protein A or protein G, respectively, which variant or fragment retains the affinity for an Fc-portion of an antibody.

The present methods comprise a step of immobilizing antibody on a solid support to provide immobilized antibodies. In some embodiments, the solid support will have the capacity to bind more antibody than the amount present in the antibody-containing sample or, in other words, the amount of antibody bound to the solid support following the immobilization step will be less than the capacity of the solid support. Because the samples generally vary with respect to antibody quantity, there will be corresponding variability in the amount of immobilized antibody from one sample as compared to another.

In some other embodiments, it might be desirable to limit the quantity of bound antibody and the solid support will only have the capacity to bind up to a certain amount of antibody (e.g., up to 5 µg, up to 10 µg, or up to 15 µg of protein). In these embodiments, although there will be a limit as to the maximum amount of antibody that can be bound to the solid support, there may still be variability in the amount of immobilized antibody in one sample as compared to another. This is because one or more of the samples might contain a small quantity of antibody, less than the maximum loading capacity of the solid support. One approach for preparing a solid support that has limited capacity for binding antibody is to make a very low-capacity resin such that a larger volume of resin slurry (20 uL for example) contains only enough capacity to bind 5 ug of antibody. An alternative approach is to reduce the effective capacity of a resin by diluting the resin with an appropriate volume of non-functionalized resin. For example, a protein G-sepharose resin with a binding capacity of 20 ug/uL could be converted to a mixed resin with an effective binding capacity of 0.5 ug/uL by mixing 1 part of protein G-sepharose with 40 parts unfunctionalized sepharose. In performing such a resin dilution, in some embodiments, the diluent will be a resin which is constructed from the same base material as the affinity resin, has pore sizes small enough to exclude antibodies, and lacks any surface functionality which may interact with antibodies or the chemical reagents used to prepare antibody conjugates.

In some aspects of the invention, antibodies are immobilized on a solid support by the step of applying an antibody-containing sample to a solid support. If desired, a washing step can be performed following immobilization to separate the immobilized antibodies from the cell culture supernatant or other components of the antibody-containing samples.

Once the antibodies are immobilized on the solid support, a reduction step is performed in order to fully reduce the reducible disulfide bonds of the immobilized antibodies and to generate reactive thiols. The antibodies are reduced under conditions that are favorable to a complete reduction of the reducible disulfide bonds. Typically, the antibodies are reduced with an excess of reducing agent in order to ensure a substantially complete reduction of the reducible disulfide bonds. By the phrase "fully reducing the reducible disulfide bonds of the antibody" it is meant that substantially all (e.g., greater than 70%, preferably greater than 80%, even more preferably greater than 85%, 90%, or 95%) of the antibodies in a sample are fully reduced as to their reducible disulfide bonds. In other words, for a substantial amount of the antibodies in a sample, all of the antibodies' reducible disulfide bonds will be cleaved during the reduction step. For example, if the antibodies in a sample have 4 reducible disulfide bonds, after the reduction step, all 4 reducible disulfide bonds of a substantial amount of the antibodies will be cleaved to generate 8 reactive thiols. The reduction is one that is selective for reducible disulfide bonds. By the phrase "selective for reducible disulfide bonds" it is meant that the reducible disulfide bonds are substantially the only bonds that are reduced. In some embodiments of the invention, the reducible disulfide bonds are the naturally occurring interchain disulfides of the antibody, the antibodies are reduced under conditions that are favorable to a complete reduction of the naturally occurring interchain disulfides, and the reduction is one that is selective for the naturally occurring interchain disulfides. By the phrase "selective for interchain disulfides" it is meant that interchain disulfides are selectively reduced. In other words, the interchain disulfides are substantially the only bonds that are reduced. Because the antibodies are contacted with an excess of reducing agent and the reducing agent is selective for the reducible disulfide bonds, the generation of reactive thiols per antibody will generally be independent of the quantity of antibody in the sample.

In one aspect, the reducing agent used in the reduction step is TCEP (tris(2-carboxyethyl)phosphine) and the TCEP is added at an excess for 30 minutes at room temperature. For example, 250 uL of a 10 mM solution of TCEP at pH 7.4 will readily reduce the interchain disulfides of 1 to 100 ug of antibody in 30 minutes at room temperature. Other reducing agents and conditions, however, can be used. Examples of other reducing agents include DTT (dithiothreitol), mercaptoethanol and mercaptoethylamine. Examples of reaction conditions include temperatures from 5° C. to 37° C. over a pH range of 5 to 8. Conjugation of the resulting antibody thiols and analysis by hydrophobic interaction or reversed-phase chromatography (for examples, see FIGS. 1 and 3 respectively) provides an indicator of the extent of disulfide reduction achieved under various reducing conditions. Following the reduction, a washing step can be performed in order to remove reducing agent and any other components that may have nonspecifically attached to the solid support during the antibody capture step, for example, culture media components.

In some aspects of the present invention, although the samples will vary with respect to antibody quantity and antibody sequence, the majority of antibodies will not vary substantially with respect to the number of reducible disulfide bonds. For example, in some embodiments, substantially all of the antibody contained in the first and second sample will have the same amount of reducible disulfide bonds. In some such embodiments, the reducible disulfide bonds will be interchain disulfides. If the antibody in the first and second sample have 4 interchain disulfide bonds (e.g., human IgG1), after reduction, the reduced immobilized antibodies in both samples will each have 8 reactive thiols. This level of reduction to 8 reactive thiols per antibody is independent of the quantity of antibody in the samples due to the excess of reducing agent, the selectivity of the reduction step, and the uniform number of reducible bonds on each antibody. Similarly, if the antibody in the first and second sample have 5 interchain disulfide bonds, after reduction, the reduced immobilized antibodies in both samples will each have 10 reactive thiols. This level of reduction to 10 reactive thiols per antibody is also independent of the quantity of antibody due to the excess of reducing agent, the selectivity of the reduction step, and the uniform number of reducible disulfides on each antibody. In some embodiments wherein a panel of murine antibodies is being screened, e.g., a panel of murine antibodies from hybridomas, a majority of the antibodies will be either one of the major murine isoforms IgG1 and IgG2a. Murine IgG1 and IgG2a isoforms both contain 5 interchain disulfide bonds and after reduction, each antibody will have 10 reactive thiols. Accordingly, a majority of the antibodies will have the same amount of reducible disulfide bonds. Although the majority of isoforms in these embodiments may be IgG1 and IgG2a, other isoforms may be present as well. For example, murine IgG2b, murine IgG2c and murine IgG3 isoforms may be present as well. In instances where murine IgG2b isoforms are present, the reduction of these antibodies will generate 12 reactive thiols as IgG2b isoforms have 6 interchain disulfide bonds. In some embodiments, transgenic mice will be used for antibody production and the mice can be genetically engineered to produce antibodies having a certain isotype as well as antibodies having human IgG isotypes. In some such embodiments, the mice can be engineered to only express specific isotypes. In some embodiments, the mice can be engineered to only express only one isotype or one or two major isotypes.

Following the reduction step, the antibodies are loaded with the desired chemical entity (in other words, conjugated to the desired chemical entity). The selection of the chemical entities to be used depends in part on the purpose of the assay. In some embodiments, the antibodies will be screened for the purpose of selecting an antibody for use as an ADC. In these embodiments, it is desirable for the antibodies to be conjugated to a drug. The antibodies can be conjugated directly to the drug or indirectly via a linker. The drug and drug-linker can be any drug or drug-linker that is effective for use as an ADC and that is thiol reactive. By the phrase "thiol reactive" it is meant that the chemical entity will react with a reactive thiol generated by reduction of a reducible disulfide bond and will form a covalent bond thereto. Thiol reactive drugs and drug-linkers include those drugs or drug-linkers that aren't naturally thiol reactive but have been derivatized with a thiol reactive agent to render them thiol reactive. The conditions used for conjugation are such that the drug will selectively react with a reactive thiol (either directly or through its linker). Examples of thiol reactive groups that are highly selective for reactive thiols include, for example, maleimides, such as N-ethylmaleimide. Maleimides such as N-ethylmaleimide are considered to be fairly specific to sulfhydryl groups, especially at pH values below 7, where other groups are protonated. At pH 7, for example, the reaction with simple thiols is about 1,000 fold faster than with the corresponding amines. Reactions of thiols with maleimides are very rapid at room temperature at pH 7.4, and 30 minutes is adequate to ensure complete reaction without risking conjugation of the maleimide to amine groups. Accordingly, in some embodiments, the drug will be linked to the antibody via a maleimide group. Other reactive groups that are highly selective for reactive thiols include, for example, iodoacetamides, vinyl sulfones, and aziridines.

In some embodiments, it will be desirable to fully load an antibody with drug. In such embodiments, the desirable drug loading level will be equal to the number of reactive thiols per antibody. For example, in some such embodiments, the desired drug loading will be 10 drugs per antibody and the number of reactive thiols per antibody will be 10. In some embodiments wherein a drug loading level which is equal to the number of reactive thiols is desired, the thiol reactive drug or drug-linker will be provided in sufficient excess to the immobilized antibodies in order to react with all of the available reactive thiols. Because the reaction is set up such that the drugs and drug-linkers to be used in this step are thiol reactive and the conditions used are selective for conjugation to reactive thiols, the drug or drug-linker selectively reacts with the reactive thiols (i.e., the drug and drug linkers do not substantially react with other sites on the antibody, including for example, other amino acids (e.g, lysine residues)). Because of this selectivity, it is possible to control the drug loading and to design the experiment such that there will be a substantial uniform drug loading between samples. By the phrase "substantial uniform drug loading between samples" it is meant that the average drug loading between samples is substantially the same or, in other words, the average number of drug molecules per antibody in sample one will be substantially the same as the average number of drug molecules per antibody in sample two. Some variance in drug loading can be expected but generally it will be within a variance of about 25%, preferably within a variance of 20% or even 10%. Accordingly, in some embodiments where a majority of the samples contain antibodies of the murine IgG1 and IgG2a subtypes, if a thiol reactive drug or drug-linker is added to the samples in sufficient excess to react with all of the available reactive thiols, there will be an average of 10 drug molecules per antibody in the majority of samples. Because these samples have a substantial uniform drug loading, once eluted, the concentration of the purified ADCs can be determined by methods known in the art, e.g., spectrophotometric methods, and their activities can be compared to determine which antibodies are more or less active in an assay. This comparison can be performed even if the antibodies to be compared are provided at variable concentrations and in some embodiments, at unknown variable concentrations. A comparison between antibodies provided at unknown variable concentration is aided by the ability to substantially uniformly load them with drug or drug-linker.

In some embodiments, it is not desirable to fully load an antibody with drug or drug-linker. In some such embodiments, if a lower drug loading level is desired, the immobilized antibodies can be reacted with both a drug or drug-linker and a thiol capping agent. The term "thiol capping agent" is used herein to refer to an agent which selectively blocks a reactive thiol. The drug or drug-linker and thiol capping agent will be provided in a ratio of drug or drug-linker to thiol capping agent which results in the desired drug loading. Like the drug or drug-linker, the capping agent will be highly selective for reactive thiols. Thiol reactive capping agents include those capping agents that aren't naturally thiol reactive but have been derivatized with a thiol reactive agent to render them thiol reactive. Examples of thiol capping agents that can be used include maleimide capping agents such as, for example, N-ethyl maleimide. Other capping agents include, for example, iodoacetamide and iodoacetic acid. In some embodiments, both the drug or drug-linker and thiol capping agent have the same type of thiol reactive agent. For example, in some preferred embodiments, if the drug is to be linked to the antibody via a maleimide group, the capping agent will also be linked to the antibody via the same type of maleimide group. This helps ensure that the relative reaction rates of the drug-linker and capping agent are similar. Preferably, there will be no more than about a 100-fold different in the relative reaction rates, more preferably no more than 10-fold, and even more preferably no more than 5-fold difference in the relative reaction rates.

In one aspect, the ratio of capping agent and drug or drug-linker chosen will be dependent on the desired level of drug loading. In some embodiments, the ratio of drug linker or drug to capping agent provided to the immobilized antibodies will be reflected in the ratio at which these reagents are conjugated to the antibodies. In embodiments when the drug or drug-linker and capping agent are provided in molar excess, the ratio of drug linker or drug to capping agent provided will be reflected in the ratio at which these reagents are conjugated to the antibodies if the intrinisic thiol reaction rates of these two components are the same. For example, if a reaction mixture to be used for conjugation has a 1:1 mixture of drug linker or drug to capping agent, in embodiments where the instrinsic thiol reactive rates of the drug or drug-linker and capping agent are the same and a majority of the samples comprise antibodies having 5 reducible disulfide bonds (e.g., antibodies of the murine IgG1 and IgG2a subtypes), following the reaction, there will be an average of 5 drug molecules per antibody and 5 capping agents per antibody in the majority of samples. It has been observed, however, by the present inventors that the instrinsic thiol reaction rates of the drug or drug-linker and capping agent are generally not the same, and consequently, if the drug or drug-linker and capping agent are provided in excess, the ratio at which the drug or drug-linker and capping agent are provided to the samples comprising immobilized antibodies will not be same ratio at which they are conjugated to the antibodies. In such embodiments, the appropriate ratio of drug or drug-linker to capping agent can be determined experimentally in order to achieve the desired level of drug loading. Notably, as long as the drug or drug-linker and capping agent are provided in excess (generally, an excess of at least about 3-fold) and the antibodies present in the samples have substantially the same number of reducible disulfide bonds, the ratio will produce consistent (i.e., substantially uniform) levels of drug loading across samples regardless of quantity of antibody present on the solid support.

In some preferred embodiments, the conjugation reaction of the antibody to the drug or drug-linker and capping agent will be under kinetic control, not thermodynamic control. For example, under conditions in which the total moles of drug or drug-linker and capping agent provided to a sample containing the immobilized antibodies is equal to or less than the number of moles of reactive thiol in the sample, then the ratio of drug or drug-linker and capping agent provided to the sample comprising the immobilized reduced antibodies will be reflected in the actual conjugation ratio of the antibodies to drug or drug-linker and capping agent. Such a conjugation reaction can be said to be under thermodynamic control. For example, if 100 pmoles of a murine IgG1 antibody (about 15 ug) were reduced with excess reducing agent to produce 10 thiols per antibody, then 1 nmole of reactive thiol would be present. If a 1:1 mixture of drug or drug-linker to capping agent were prepared such that the concentration of each was 0.5 mM and the total concentration was 1 mM, the addition of 1 uL of this solution to the reduced antibody would present a total of 1 nmole of drug or drug-linker and capping agent. Assuming the drug or drug linker and capping agent and thiol reaction is a highly favorable one (for example, both of the drug or drug-linker and capping agents are maleimido derivatives), the conjugate prepared by this procedure would have a 1:1 mixture of the two compounds (the thiol-maleimide reaction is highly favorable and thermodynamics would effectively drive this reaction to completion). This would be true even if one of the compounds reacted at a substantially faster rate than the other. In embodiments where it is desirable for a plurality of sampes to be uniformly loaded, this approach would generally require that the quantity of antibody present in each of the samples be known. Moreover, in embodiments where there is variability in the amount of antibody between samples (such as a panel of antibodies from hybridomas), it would require a great deal of effort to tailor the quantity of drug or drug linker and capping agent to be added to each sample in order to arrive at samples that are substantially uniformly loaded. In embodiments where the quantity of antibody in the samples is unknown and/or there is variability between samples, it is generally preferable to manipulate the reaction so that it is under kinetic control and accordingly, to provide the antibody-containing samples with an excess of total drug or drug-linker and capping agent.

In some embodiments of the present invention, the chemical entities to be conjugated to the reactive thiols of the reduced antibodies will be provided in molar excess (molar excess as to the reactive thiols). In these embodiments, if the drug or drug-linker reacts more quickly with a reactive thiol than the capping agent, the drug or drug-linker will be disproportionately represented on the final conjugate. This is because the drug or drug linker and capping agent are effectively competing with each other to react with a limiting number of available reactive thiols. If the drug or drug linker and capping agent are present at equal concentrations in the reaction solution, they will only be conjugated at equal concentrations if their reaction rates are the same. By altering the composition of a reaction mixture such that the concentrations of the drug or drug linker and capping agent are not equal, the ratio at which they react with the available thiols can be controlled. For example, a slow-reacting drug or drug linker will be disproportionately underrepresented on a conjugate prepared with a 1:1 mixture with a faster reacting capping agent. By changing the ratio to 2:1 in favor of the slower reacting drug or drug-linker, its representation on the conjugate will be increased. Thus, by the modulation of the ratio of drug or drug linker and capping agent provided to the samples comprising the immobilized reduced antibodies, a desired ratio of drug or drug linker and capping agent on the final conjugate can be achieved. Under conditions in which the total drug or drug linker and capping agent is present in excess relative to the available reactive thiols, their distribution on the final product will be independent of the starting thiol quantity. In this manner, a plurality of samples can be substantially uniformly loaded even when the quantity of antibody in the samples is unknown and/or there is variability between samples. In some embodiments, an appropriate volume of drug or drug-linker and capping agnet is provided to the samples such than a molar excess of about 2 fold (and, even more preferably, a molar exces of 3-fold or more) of total reactants relative to total thiols is present. If the quantity of antibody in the samples is unknown, each sample can be treated as if it has the maximum amount of antibody. For many of the samples, significantly less than the maximum amount will be present and the excess will be greater than 2 fold. This provision of excess reactants having a set ratio allows for variable quantities of antibodies across a panel to be treated with a large, fixed quantity of total drug or drug linker and capping agent to produce a panel of conjugates with comparable loading of each drug or drug linker and capping agent present. The fact that equal treatment of samples results in comparable levels of loading, regardless of the quantity of antibody initially present in the sample, makes this method convenient for high-throughput applications in which large numbers of antibodies are conjugated.

As discussed herein, although it is preferable that a majority of the samples to be assayed do not vary with respect to the number of reducible disulfide bonds present on the antibodies contained therein, in some embodiments, there will be some variation. In some embodiments, despite the variation, the samples will be treated with the same ratio of chemical entities. When interpreting the data, the skilled artisan will recognize that a certain subset of the samples differed in the amount of reducible disulfide bonds. If desired, the skilled artisan can determine the antibody isotype prior to or post conjugation to aid in data interpretation.

In some embodiments, prior to the conjugation step, standard methods can be used to determine the antibody isotype in each of the samples and therefore, the number of reducible disulfide bonds per antibody in each of the samples. In some such embodiments, samples that contain antibodies having the same number of reducible disulfide bonds will be contacted with a reaction mixture having one ratio of drug or drug linker to capping agent to arrive at a desired drug loading and samples that contain antibodies having a differing number of reducible disulfide bonds will be contacted with a reaction mixture having a different ratio of drug or drug linker to capping agent to arrive at that same desired drug loading. For example, in some embodiments, if the desired average drug loading is 4, samples that contain antibodies of murine IgG1 and IgG2a (10 reactive thiols per antibody when fully reduced) will all be contacted with a reaction mixture having a ratio of drug or drug linker to capping agent to arrive at an average drug loading of 4 and average capping agent loading of 6. Samples that contain antibodies of murine IgG2b (12 reactive thiols per antibody when fully reduced) will be contacted with a reaction mixture having a different ratio of drug or drug linker to capping agent (e.g., a higher fraction of capping agent) to arrive at the same average drug loading of 4. In other embodiments, although there may be variation between isotypes and number of interchain disulfides, it will be accepted that there will be some variation in loading and all of the samples will receive the same ratio of drug or drug linker to capping agent.

In some embodiments, prior to the conjugation step and following the reduction step, there will be a partial reoxidation step. For example, in some embodiments, the reducible disulfide bonds will consist of naturally occurring interchain disulfide bonds as well as disulfide bonds formed from introduced sulfhydryl groups. In some of these embodiments, it will be desirable to conjugate the selected chemical entities to the introduced sulfhydryls but not to the sulfhydryl groups of the naturally occurring interchain disulfide bonds. In these embodiments, following the complete reduction of the reducible disulfide bonds, there can be a partial reoxidation step to reoxidize the naturally occurring interchain disulfide bonds leaving the introduced sulfhydryls available for binding to the desired chemical entities. Reoxidation of the native disulfides can be achieved, for example, by treatment of the reduced antibodies with a large molar excess of dehydroascorbic acid at pH 6.5, with the reaction allowed to proceed for 1 hour at room temperature.

In any of the embodiments described herein, instead of, or in addition to the capping agent, a detection agent is provided for conjugation. The detection agents can be, for example, primary labels or secondary labels. In some embodiments, the detection agent will be one that is detected directly. In other embodiments, the detection agent will be one that is detected indirectly. In some embodiments, the detection agent will be, for example, any thiol reactive label that can be used for antibody quantiation and/or as a reporter for a binding assay or any other desirable assay. Thiol reactive labels include those labels that aren't naturally thiol reactive but have been derivatized with a thiol reactive agent to render them thiol reactive. In some embodiments, the same type of thiol reactive agent will be used to link the various chemical entities (detection agent and/or drug or drug-linker and/or capping agent) to the antibody. In some embodiments, the detection agent will be a radioactive compound, a chemiluminescent agent, a fluorescent agent, or a chromogen. In some embodiments, the detection agent will be a fluorescent molecule such as a fluorophore. In some embodiments, the detection agent will be biotin. In one aspect, the detection agent will be a fluorophore and the fluorophore will be derivatized with a maleimide group in order to make it thiol reactive. The teachings described herein can be used to assess the preferred loading level of a select detection agent. In some embodiments, a fluorophore is used as the detection agent and the fluorophore is loaded at an average loading of about 2.5 to about 3 fluorophores per antibody. Examples 3 and 4 provide exemplary descriptions of how to tailor the ratio of chemical entities in order to achieve a desired drug and/or fluorophore loading level.

The present invention encompasses embodiments wheren the antibodies are screened not for the purpose of selecting an antibody for use as an ADC but for the purpose of selecting an antibody for use as an unconjugated antibody. In these embodiments, immobilized antibodies will be contacted with a detection agent and capping agent at a selected ratio and there will be no use of drug or drug-linker. Using the teachings described herein, including the teachings of examples 3 and 4, the appropriate ratio of detection agent to capping agent can be determined.

After contacting the reduced antibodies with the appropriate amount and type of chemical entities (selection of the chemical entities will be dependent, for example, on whether it is desired to screen antibodies as unconjugated antibodies or ADCs; whether it is desired to have a full drug loading or partial drug loading; and whether it is desired to include a detection agent in the mix) and allowing sufficient time for completion of the reaction (e.g., 30 minutes for maleimide-containing chemical entities), it is desirable to perform a washing step in order to remove any unreacted materials. Subsequently, the immobilized antibody conjugates can be eluted from the solid support to provide antibody conjugate compositions. Methods of eluting proteins from solid supports are known in the art and the skilled practitioner will be able to select an appropriate buffer for elution. For example, in embodiments, where the solid support comprises protein A or protein G resin, the antibody conjugates can be eluted with standard low pH buffers for elution from protein A or protein G columns.

In some embodiments of the invention, the methods described herein for making antibody conjugates will result in a plurality of antibody drug conjugate compositions having substantially uniform drug loading (the skilled artisan will understand that there may be some outliers depending on the uniformity of number of reducible disulfide bonds across samples). In these embodiments, because of the substantially uniform drug loading between samples, the relative characteristics of antibodies in a first and second sample can be compared. This comparison can be performed even though the antibodies to be compared were provided at variable concentrations and, in some embodiments, at unknown variable concentrations. A comparison between the antibodies of unknown and variable concentration is made easier with the ability to substantially uniformly load them with drug or drug-linker.

Methods for determining drug loading are known in the art. One method that is used herein is high-performance liquid chromatography on a polystyrene divinylbenzene copolymer, e.g., a reversed-phase PLRP™ column. This denaturing technique can cleanly separate the variously loaded light chain and heavy chain species. Hydrophobic interaction chromatography (HIC) can also be used as an analytical method used to determine isomeric mixtures from resultant conjugates. The drug loading level can be determined based on a ratio of absorbances, e.g., at 250 nm and 280 nm. See, for example, U.S. Publication No. 20090010945.

In some embodiments, following elution of the antibody conjugates, activity assays and/or other assays will be performed in order to characterize the antibody conjugates. In some embodiments, cell binding, affinity, and/or cytoxicity assays will be performed. Many methods of determining whether an ADC binds a target of interest or exerts a cytotoxic effect on a cell are known to those of skill in the art, and can be used in the present methods. For example, cell viability assays can be used to determine the cytotoxic effect of an ADC on a cell. See, for example, U.S. Pat. Nos. 7,659,241 and 7,498,298, each of which is incorporated herein in its entirety and for all purposes, for exemplary cell binding and cytotoxicity assays.

In some embodiments, following elution of the antibody conjugates, it will be desirable to determine the quantity of antibody or antibody conjugate in the antibody conjugate compositions. In some embodiments, it will be desirable to determine the actual quantity of antibody or antibody conjugate in a sample. In other embodiments, it will be sufficient to determine the relative quantity of antibody or antibody conjugate in a plurality of samples. For example, it may be sufficient to know that sample 1 has more antibody than sample 2 which has more antibody than sample 3, and so forth. Many methods for determining protein quantity are known in the art and can be used herein. In some embodiments, an absorbance assay will be used to determine antibody concentration. In embodiments where a fluorophore is part of the antibody conjugate, antibody concentration can be determined using a fluorescence assay. In embodiments where fluorescence is used for protein quantitation, a standard may be necessary to convert the raw fluorescence values into a concentration. Methods of using fluorescence and generating standard curves to determine protein concentration are known in the art. In one example, approximately 200 µg of a standard antibody will be conjugated during the conjugation step after being spiked into blank media. After elution, the concentration of this standard will be determined by conventional methods, e.g., a conventional A280 absorbance assay, and a standard curve prepared by a dilution series will be assayed for fluorescence alongside the conjugate samples. Alternatively, a liquid-handling robot can be used to normalize plates thereby eliminating the need for serial dilutions.

In some embodiments, the results of a cytotoxicity assay and knowledge of the relative or actual antibody concentration in the antibody conjugate compositions will be used to identify antibodies with desired characteristics. The methods described herein for making antibody conjugates allow for comparisons to be made between a plurality of antibodies of varying concentration and, in some embodiments, unknown quantity. The methods described herein for making antibody conjugates allow for a selection of antibodies with desirable characteristics when starting with, for example, a panel of antibodies resulting from a hybridoma fusion. In some preferred embodiments, it is the substantial uniform drug loading between samples that allows for relevant comparisons to be made between samples. Failure to ensure substantially uniform loading levels, could, for example, lead to erroneous results from a screen of a panel of antibodies for use as ADCs. This is because it would not be known if an ADC sample exhibited greater cytotoxicity because of the characteristics of the antibody as an ADC or because the sample contains more drug per antibody. For example, an antibody conjugate composition comprising antibody "A" and having an average drug loading of 4 would typically be expected to exhibit more cytotoxicity than an antibody conjugate composition comprising antibody "B" and having an average drug loading of 1. This greater cytotoxicity would not be an indicator of the relative characteristics of antibodies A and B as ADCs, but simply an indicator of the greater drug loading on antibody A. If both antibody conjugate compositions had an average drug loading of about 4, if one showed greater cytotoxicity, it could be attributed to the antibody and not simply the drug loading. Similarly, the ability to determine the actual or relative quantity of antibody or antibody conjugate in the samples also allows for relevant comparisons to be made between samples. Without knowledge of actual or relative quantity of antibody or antibody conjugate in the sample, it would not be known if an ADC exhibited greater cytotoxicity because of the particular antibody or simply because there is more antibody or ADC in the sample.

In addition to providing methods for making antibody conjugates for use in antibody screening assays and antibody conjugates produced by the claimed methods, the present invention provides antibodies and/or antibody conjugates (e.g., antibody drug conjugates) for therapeutic use wherein the antibody was selected using the methods described herein.

As previously discussed, the drug or drug-linker used in the present methods can be any drug or drug-linker that is effective for use as an ADC and that is thiol reactive. The drug can be any cytotoxic, cytostatic or immunosuppressive drug. Methods of selecting drug and drug-linker for use as ADCs are known in the art. See, for example, WO 2004010957, WO 2007/038658, U.S. Pat. Nos. 6,214,345, 7,498,298, and U.S. Publication No. 2006/0024317, each of which is incorporated herein by reference in its entirety and for all purposes.

Useful classes of cytotoxic or immunosuppressive agents include, for example, antitubulin agents (e.g., auristatins, maytansinoids, vinca alkaloids), topoisomerase inhibitors (e.g., camptothecins), DNA minor groove binders (e.g., calicheamicins, duocarmycins, enediynes, lexitropsins, chloromethylbenzindolines), DNA replication inhibitors (e.g., anthracyclines), alkylating agents (e.g., platinum complexes such as cis-platin, mono(platinum), bis(platinum) and tri-nuclear platinum complexes and carboplatin), protein kinase inhibitors, cytotoxic enzymes, and protein toxins.

In some embodiments, suitable cytotoxic agents include, for example, antibiotics, antifolates, antimetabolites, chemotherapy sensitizers, etoposides, fluorinated pyrimidines, ionophores, nitrosoureas, platinols, pre-forming compounds, purine antimetabolites, radiation sensitizers, steroids, puromycins, doxorubicins, and cryptophysins.

Individual cytotoxic or immunosuppressive agents include, for example, an androgen, anthramycin (AMC), asparaginase, 5-azacytidine, azathioprine, bleomycin, busulfan, buthionine sulfoximine, gamma calicheamicin, N-acetyl gamma dimethyl hydrazide calicheamicin, camptothecin, carboplatin, carmustine (BSNU), CC-1065, cemadotin, chlorambucil, cisplatin, colchicine, cyclophosphamide, cytarabine, cytidine arabinoside, cytochalasin B, dacarbazine, dactinomycin (formerly actinomycin), daunorubicin, decarbazine, discodermolide, docetaxel, doxorubicin, morpholino-doxorubicin, cyanomorpholino-doxorubicin, echinomycin, eleutherobin, epothilone A and B, etoposide, estramustine, an estrogen, 5-fluordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, netropsin, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16 and VM-26.

In some embodiments, the drug is an anti-tubulin agent. Examples of anti-tubulin agents include, but are not limited to, taxanes (e.g., Taxol® (paclitaxel), Taxotere® (docetaxel)), and vinca alkyloids (e.g., vincristine, vinblastine, vindesine, and vinorelbine). Other antitubulin agents include, for example, baccatin derivatives, taxane analogs (e.g., epothilone A and B), nocodazole, colchicine and colcimid, estramustine, cryptophysins, cemadotin, combretastatins, discodermolide, and eleutherobin.

In certain embodiments, the cytotoxic agent is a maytansinoid, another group of anti-tubulin agents. For example, in specific embodiments, the maytansinoid is maytansine or DM-1 or DM-4 (ImmunoGen, Inc.; see also Chari et al., 1992, Cancer Res. 52:127-131).

In some embodiments, the drug is an auristatin, another group of anti-tubulin agents. Auristatins include, but are not limited to, auristatin E and derivatives thereof. AFP, AEB, AEVB, MMAF, and MMAE are examples of auristatins that can be used herein. The synthesis and structure of auristatins are described in U.S. Patent Application Publication Nos.

2003-0083263, 2005-0238649 and 2005-0009751; International Patent Publication No. WO 04/010957, International Patent Publication No. WO 02/088172, and U.S. Pat. Nos. 7,498,298, 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated herein by reference in its entirety and for all purposes.

Exemplary linkers that can be used with the present methods are described in WO 2004010957, WO 2007/038658, U.S. Pat. Nos. 6,214,345, 7,659,241, 7,498,298 and U.S. Publication No. 2006/0024317, each of which is incorporated herein by reference in its entirety and for all purposes.

In some exemplary embodiments of the present invention, the drug-linker is of Formula I or Formula II wherein Val-Cit refers to the dipeptide valine-citrullline Formula I

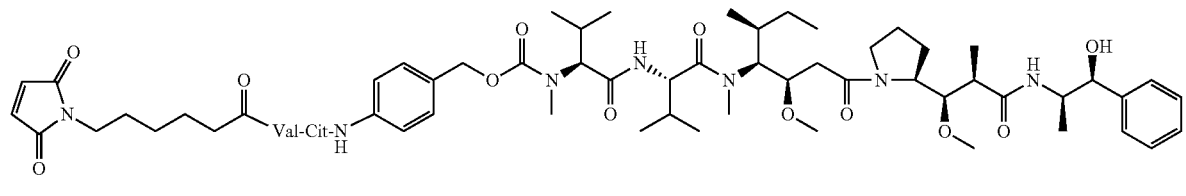

("vc-MMAE")

Formula II

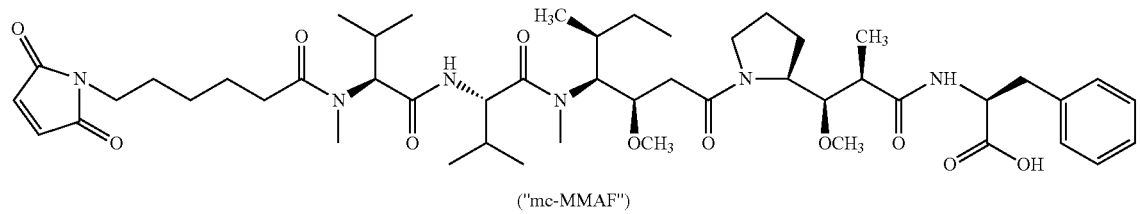

("mc-MMAF")

The linker part of a drug-linker is a compound that can be used to link the antibody to the drug. The linker can comprise more than one chemical moiety. In some embodiments, the linker is cleavable under intracellular conditions, such that cleavage of the linker releases the drug unit from the antibody in the intracellular environment. In some embodiments, the linker is a peptidyl linker (e.g. a linker that comprises two or more amino acids) that is cleaved by an intracellular peptidase or protease enzyme, including, but not limited to, a lysosomal or endosomal protease. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). In some embodiments, the peptidyl linker cleavable by an intracellular protease comprises a Val-Cit dipeptide or a Phe-Lys dipeptide (see, e.g., U.S. Pat. No. 7,659,241, incorporated by reference herein in its entirety and for all purposes). In yet other embodiments, the linker is not cleavable and the drug is released by antibody degradation.

In some embodiments, the cleavable linker is pH-sensitive, i.e., sensitive to hydrolysis at certain pH values and/or cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

Proteins

The methods described herein for making antibody conjugates can also be used to make fusion proteins for use in fusion protein screening assays. The term "fusion protein" is used herein to refer to binding domain-Ig fusions, wherein the binding domain may be, for example, a ligand, an extracellular domain of a receptor, a peptide, a non-naturally occurring peptide or the like with the proviso that the binding domain does not include a variable domain of an antibody. Like the antibodies described herein, the Ig portion of the fusion protein must comprise at least one reducible disulfide bond, and a domain capable of binding to a solid phase. In one aspect, the Ig domain will be the Fc region of an antibody. Examples of domain-Ig fusion proteins include etanercept which is a fusion protein of sTNFRII with the Fc region (U.S. Pat. No. 5,605,690), alefacept which is a fusion protein of LFA-3 expressed on antigen presenting cells with the Fc region (U.S. Pat. No. 5,914,111), a fusion protein of Cytotoxic T Lymphocyte-associated antigen-4 (CTLA-4) with the Fc region (J. Exp. Med. 181:1869 (1995)), a fusion protein of interleukin 15 with the Fc region (J. Immunol. 160:5742 (1998)), a fusion protein of factor VII with the Fc region (Proc. Natl. Acad. Sci. USA 98:12180 (2001)), a fusion protein of interleukin 10 with the Fc region (J. Immunol. 154:5590 (1995)), a fusion protein of interleukin 2 with the Fc region (J. Immunol. 146:915 (1991)), a fusion protein of CD40 with the Fc region (Surgery 132:149 (2002)), a fusion protein of Flt-3 (fms-like tyrosine kinase) with the antibody Fc region (Acta. Haemato. 95:218 (1996)), a fusion protein of OX40 with the antibody Fc region (J. Leu. Biol. 72:522 (2002)), and fusion proteins with other CD molecules (e.g., CD2, CD30 (TNFRSF8), CD95 (Fas), CD106 (VCAM-1), CD137), adhesion molecules (e.g., ALCAM (activated leukocyte cell adhesion molecule), cadherins, ICAM (intercellular adhesion molecule)-1, ICAM-2, ICAM-3) cytokine receptors (e.g., interleukin-4R, interleukin-5R, interleukin-6R, interleukin-9R, interleukin-10R, interleukin-12R, interleukin-13Ralpha1, interleukin-13Ralpha2, interleukin-15R, interleukin-21Ralpha), chemokines, cell death-inducing signal molecules (e.g., B7-H1, DR6 (Death receptor 6), PD-1 (Programmed death-1), TRAIL R1), costimulating molecules (e.g., B7-1, B7-2, B7-H2, ICOS (inducible co-stimulator)), growth factors (e.g., ErbB2, ErbB3, ErbB4, HGFR), differentiation-inducing factors (e.g., B7-H3), activating factors (e.g., NKG2D), and signal transfer molecules (e.g., gp130), BCMA, and TALI.

All of the steps described herein can easily be adapted to embodiments wherein the starting material is not antibody but fusion protein. For example, in some embodiments, fusion protein-containing samples would be provided in lieu of antibody-containing samples. The fusion protein samples would vary with respect to quantity and sequence. In preferred embodiments, substantially all of the fusion protein present in a single sample would be of the same sequence. "Substantially all of the fusion protein present in a single sample is of the same sequence" reflects the preference that a single sample contain one fusion protein with the recognition that there may be a minor amount (e.g., up to 20%, preferably less than 15%, less than 10%, less than 5%, less than 4%, or less than 3%) of contamination with another fusion protein.

As with the antibodies, the methods would not require a purification step prior to fusion protein immobilization. In some aspects, the fusion protein provided in the fusion protein-containing sample is not purified. As with the antibodies, in some embodiments, unpurifed cell culture supernatatant is provided as the fusion protein-containing sample. Methods of generating fusion proteins in cell culture are known in the art and not discussed herein. In some embodiments, fusion protein in the fusion protein-containing samples was grown in IgG depleted culture medium, and, in particular, culture medium depleted of bovine IgG. As with the antibodies, the present methods can be performed with samples that contain very small amounts (e.g., 1 to 500 µg) of fusion protein. In some embodiments, there will be from 1 µg to 100 µg, from 1 µg to 50 µg, from 1 µg to 20 µg, from 5 µg to 100 µg, from 5 µg to 50 µg, from 5 µg to 20 µg of fusion protein present in a single sample.

The present methods comprise a step of immobilizing the fusion protein on a solid support to provide immobilized fusion proteins. In some embodiments, the solid support has the capacity to bind more fusion protein than the amount present in the fusion protein-containing sample or the amount of bound fusion protein is less than the capacity of the solid support. In other embodiments, the solid support will have reduced binding capacity.

Once the fusion proteins are immobilized on the solid support, a reduction step is performed in order to fully reduce the reducible disulfide bonds of the immobilized fusion protein and to generate reactive thiols. Following the reduction step, the fusion proteins are loaded with the desired chemical entity (in other words, conjugated to the desired chemical entity). Again, the selection of the chemical entities to be used depends in part of the purpose of the assay. In some embodiments of the present invention, the fusion proteins will be screened for the purpose of selecting fusion protein for use as a fusion protein drug conjugates. In these embodiments, it is desirable for the fusion proteins to be conjugated to a drug. The fusion proteins can be conjugated directly to the drug or indirectly via a linker. The drug and drug-linker can be any drug or drug-linker described herein. As with the antibodies, the fusion proteins can be contacted with a reaction mixture comprising drug, capping agent and optionally a detection agent. As with the antibodies, the present invention encompasses embodiments wherein the fusion proteins are screened not for the purpose of selecting a fusion protein for use as an fusion protein drug conjugate but for the purpose of selecting a fusion protein for use as an unconjugated fusion protein. In these embodiments, the conjugation reaction mixture will not include a drug or drug linker but instead a mixture of detection agent and capping agent. As with the antibody conjugates, in some embodiments, the methods described herein for making fusion protein conjugates will result in a plurality of fusion protein conjugate compositions with substantial uniform loading between samples. Following elution of the fusion proteins, activity assays and/or other assays can be performed in order to characterize the fusion proteins. The results of the assays and knowledge of the relative or actual protein concentration in the fusion protein conjugate compositions can be used to identify fusion proteins that have desired properties either as unconjugated fusion proteins or as fusion protein drug conjugates.

Using the methods described herein, antibodies that perform well as unconjugated antibodies and fusion proteins that perform well as unconjugated fusion proteins can be identified and can be selected for further development. In some embodiments, antibodies or fusion proteins identified by the present methods will be formulated for therapeutic and/or non-therapeutic applications. Similarly, antibodies or fusion proteins identified as those with desired activities as drug conjugates can also be selected for further development. In some embodiments, such antibodies or fusion proteins will be conjugated to the desired drug or drug-linker using known methods and will be formulated for therapeutic and/or non-therapeutic applications. In some embodiments, the antibodies, antibody drug conjugates, fusion proteins, and fusion protein conjugates will be formulated as pharmaceutical compositions and will comprise a therapeutically or prophylactically effective amount of the antibody, antibody-drug conjugate, fusion protein, or fusion protein conjugate and one or more pharmaceutically compatible (acceptable) ingredients. For example, a pharmaceutical or non-pharmaceutical composition typically includes one or more carriers (e.g., sterile liquids, such as water and oils). Water is a more typical carrier when the pharmaceutical composition is administered intravenously. Saline solutions and aqueous dextrose and glycerol solutions can also be employed as liquid carriers, particularly for injectable solutions. Suitable excipients include, for example, amino acids, starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E.W. Martin. Such compositions will typically contain a therapeutically effective amount of the protein, typically in purified form, together with a suitable amount of carrier so as to provide the form for proper administration to the patient. The formulations correspond to the mode of administration.

Typically, compositions for intravenous administration are solutions in sterile isotonic aqueous buffer. When necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. When the pharmaceutical is to be administered by infusion, it can be dispensed with an infusion bottle containing sterile pharmaceutical grade water or saline. When the pharmaceutical is administered by injection, an ampoule of sterile water for injection or saline can be provided so that the ingredients can be mixed prior to administration.

The invention is further described in the following examples, which are not intended to limit the scope of the invention.

EXAMPLES

Example 1

Reduction of Antibodies in Solution and by Solid Phase

It is well recognized that under conditions in which antibodies retain their native folded structure, TCEP readily reduces the interchain disulfides without reducing the intrachain disulfides of the immunoglobulin domains, which are inaccessible to water-soluble reagents. When an antibody is bound to protein G affinity media, this selectivity for the interchain disulfides remains unchanged. This is illustrated in FIG. 1. This figure shows chromatograms made by reducing a protein G-immobilized murine antibody with 10 mM TCEP, followed by conjugation with an excess of mc-MMAF. These chromatograms are overlaid with chromatograms of the same antibody reduced with TCEP by conventional solution chemistry and reacted with mc-MMAF. The comparable results between the standard solution method and the solid phase method indicate that the reactivity of the antibody is not significantly changed upon binding to protein G affinity media. This feature allows a large panel of antibodies to all be reduced to the same number of reactive thiols without regard to the quantity of each antibody present, by using a quantity of TCEP that is in excess to the number of reducible disulfides in the most abundant antibody. In the absence of any knowledge of how much antibody may be present, the most theoretically abundant antibody may be defined as the capacity of the affinity resin (ug antibody per uL resin) times the volume of the resin bed (uL).

Example 2

Figure 2:
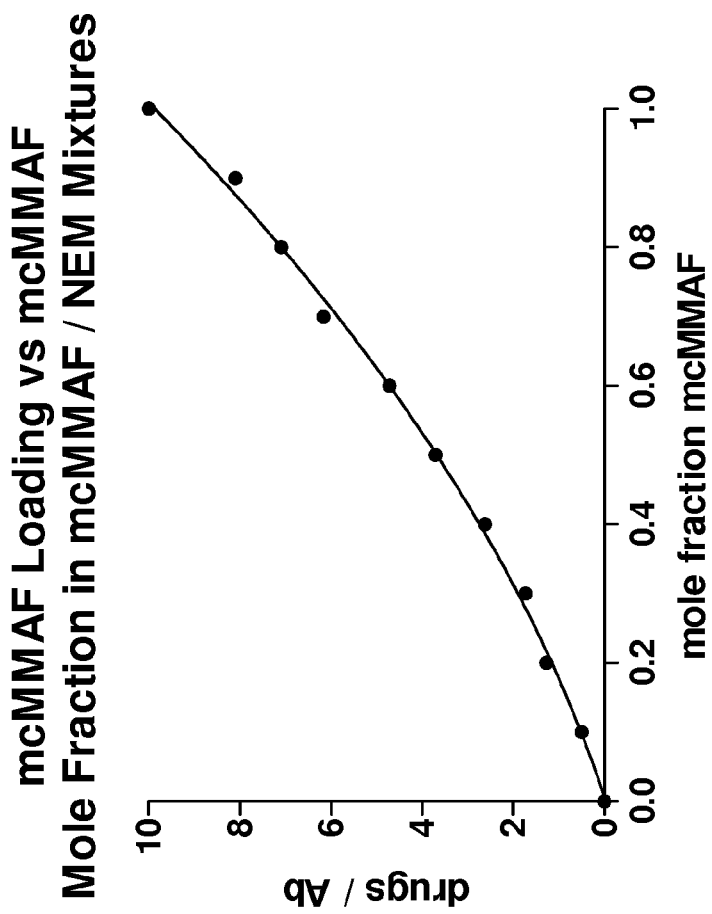
FIG. 2. This figure illustrates the mole fraction of mcMMAF in an exemplary reaction mixture comprising mcMMAF and N-ethyl maleimide necessary in order to achieve a select drug loading on a murine IgG1 murine immobilized on protein G and fully reduced with excess tris(2-carboxyethyl)phosphine.
Figure 3:
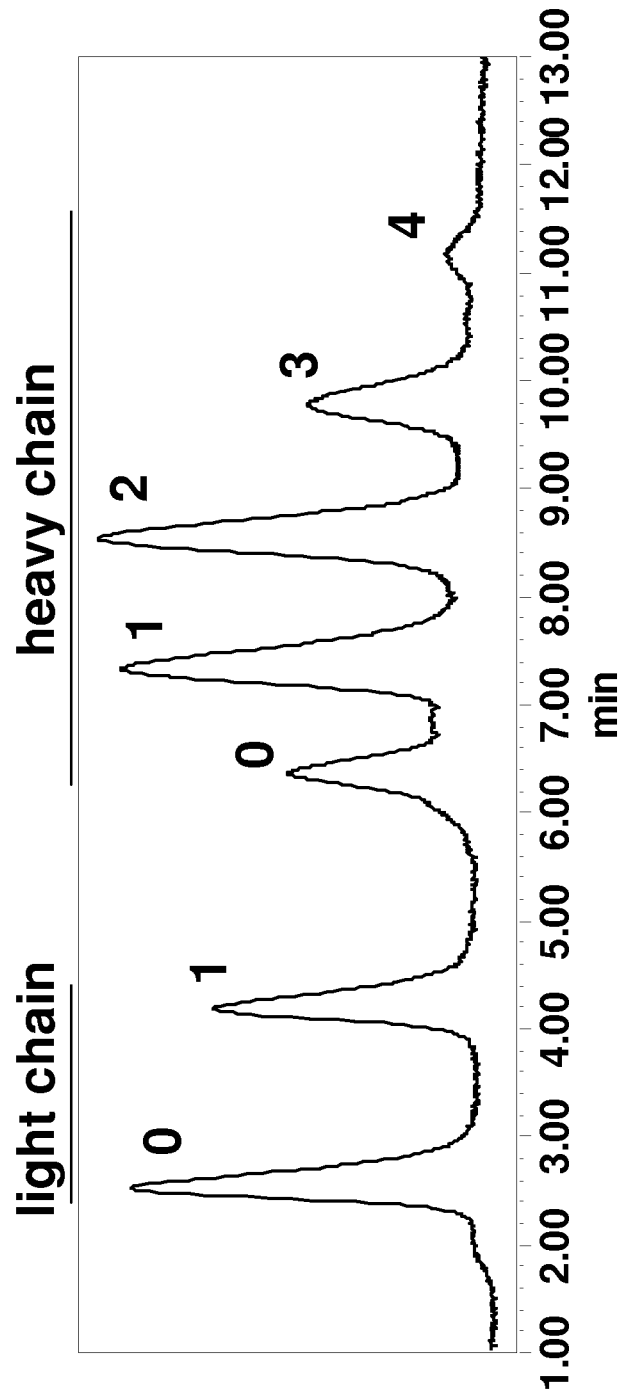
FIG. 3. The figure provides a sample PLRP chromatogram of an antibody drug conjugate illustrating the distribution of mcMMAF and NEM on the heavy and light chains of the antibody. The hydrophobicity of the drug results in later retention times for species with more drug; the number of drugs for each species is indicated.

Tailoring the Ratio of Drug to Capping Agent in the Drug Conjugation Reaction Mixture for a Desirable Drug Loading FIG. 2 illustrates the degree of loading of the maleimido drug mcMMAF when added as a mixture with N-ethyl maleimide (NEM) to a murine IgG1 immobilized on protein G and fully reduced with excess TCEP. The figure illustrates the slightly lower reactivity of mcMMAF relative to NEM, such that, in this example, if a conjugate with an average mcMMAF mole fraction of 0.4 is desired (a drug loading of 4), the mole fraction of mcMMAF in the maleimide mixture must be 0.53. The loading of mcMMAF on each conjugate was determined by reversed-phase chromatography with a PLRP-S column, which effectively separates the heavy and light chains on the basis of their drug loading; the hydrophobicity of mcMMAF results in later retention times for species with increasing degree of mcMMAF conjugation (FIG. 3). A mixture of mcMMAF and NEM was prepared at this ratio and applied to a small panel of murine antibodies to assess the generality of this ratio across different IgG isotypes. As shown in the table below, murine IgG1's and IgG2a's, both of which possess 5 interchain disulfides, gave mcMMAF drug loading levels between 3.9 and 4.2 as determined by PLRP-S chromatography. A murine IgG2b, which possesses 6 interchain disulfides, gave a correspondingly greater average mcMMAF loading as a result of the greater number of reactive thiols per antibody which result from complete reduction. This result illustrates the importance of tailoring the maleimide mixture according to the number of reducible antibody disulfides if a specific loading level is desired.

| Isotype | mIgG1 | | | | mIgG2a | | | mIgG2b |
|---------|-----|-----|-----|-----|------|-----|-----|--------|
| Drugs/Ab | 3.9 | 4.0 | 3.9 | 4.2 | 4.2 | 4.1 | 3.9 | 5.3 |

Example 3

Figure 4:
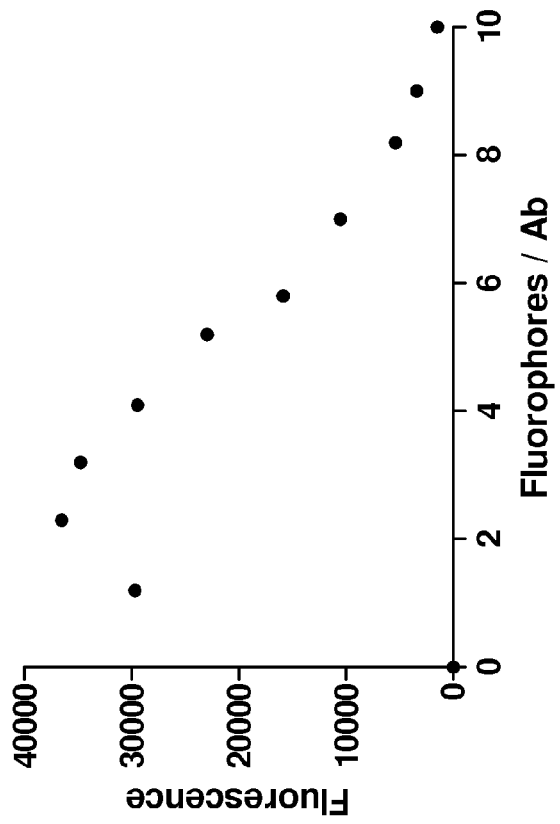
FIG. 4. This figure demonstrates the fluorescence output of drug-Alexa Fluor® 647 conjugates as a function of fluorophore loading. The number of fluorophores per antibody is plotted on the x axis and fluorescence is plotted on the y axis. Fluorescence increases rapidly to a maximum value when loading is about 2.5 to 3 fluorophores per antibody, then decreases with further loading.

Method for Determining Exemplary Fluorophore Loading Level and for Preparing a Standard for Determining Fluorophore Loading in Antibody Conjugates Mixed conjugates can be prepared with both drug and a fluorophore present on the conjugate in a controllable manner. The presence of a fluorophore can enable more sensitive quantitation of the conjugates resulting from a large panel of antibodies or as a reporter group for binding assays or other assays performed on the panel. Alexa Fluor® 647 maleimide can be included in a mixture of maleimides, along with mcMMAF and NEM, to create a panel of antibody conjugates with a desired average loading for Alexa Fluor® 647 and mcMMAF. To assess a targeted loading level of Alex-aFluor 647, a series of murine IgG1 conjugates was prepared using a binary mixture of AlexaFluor 647 maleimide and mcMMAF. The average loading of mcMMAF on these conjugates was determined by PLRP-S chromatography, and the loading of Alexa Fluor® 647 was calculated as (10–mcMMAF loading), as the total conjugation sites on fully reduced murine IgG1 is 10. The fluorescence output of these conjugates was then determined using a fluorescence plate reader, and plotted as a function of Alexa Fluor® 647 loading (FIG. 4). FIG. 4 illustrates that fluorescence rapidly increases with increasing loading level up to a maximum value corresponding to about 2.5 to about 3 fluorophores per antibody, then steadily declines with further fluorophore loading. This decrease in fluorescence output with increasing fluorophore loading is presumably due to self-quenching which arises from the close spatial proximity of the fluorophores when conjugated to the reduced disulfides of an antibody. Based on this result, a fluorophore loading of approximately 3 per antibody was selected. At this loading level not only would the fluorescence output be maximal (resulting in greatest sensitivity in fluorescent assays), but also the variation in fluorescence as a function of fluorophore loading will be minimal This will ensure that small variations in fluorophore loading across an antibody panel will not result in large differences in fluorescent output, an important point if fluorescence is to be used to quantify the conjugate concentrations.

Figure 5:
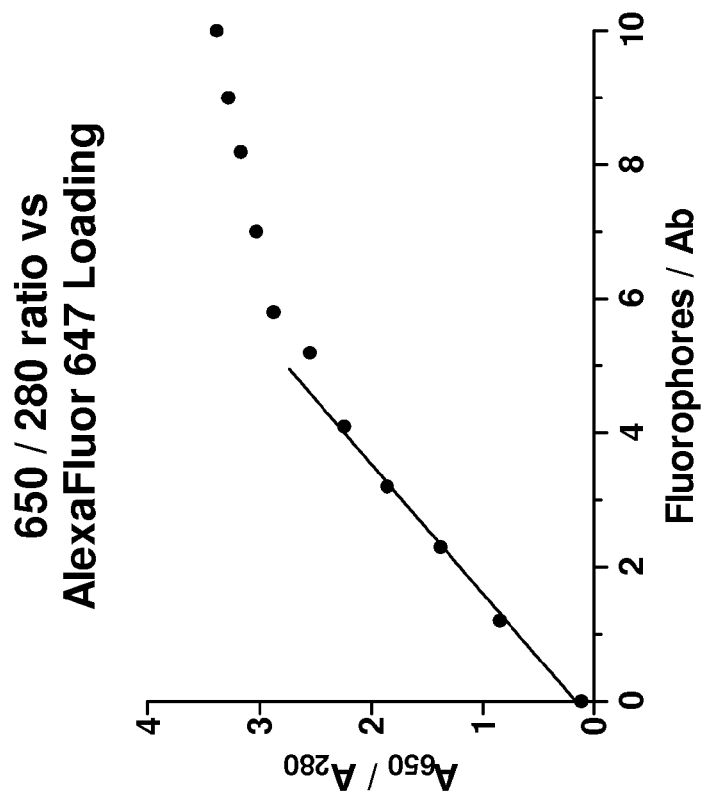
FIG. 5. This figure provides the ratio of the absorbance at 650 nm to 280 nm plotted as a function of Alexa Fluor® 647 loading level in mixed fluorophore-mcMMAF antibody conjugates.

The ratio of the absorbance at 650 nm to 280 nm was also determined for each of the fluorophore-drug conjugates described above. These ratios are shown in FIG. 5, plotted against the fluorophores per antibody data. In the region of 2.5 to 3 fluorophores per antibody, the change in the 650 nm/280 nm absorbance ratio is linear with the change in loading level, and the equation of this line can be used to determine the fluorophore loading in mixed AF647-mcMMAF antibody conjugates from the measured absorbance values.

Example 4

Exemplary Method for Tailoring the Ratio of Chemical Entities in Order to Achieve a Desired Drug Loading Level As described in example 3, an exemplary number of fluorophores per antibody is about 3. Assuming that the antibody-containing samples are of the murine IgG1 and IgG2a isotypes and the desired loading level for fluorophores is 3, a drug loading level of 7 could be achieved by preparing the appropriate mixture of AF647 maleimide and mcMMAF. However, a lower level of drug loading may be achieved by including a capping reagent such as N-ethyl maleimide (NEM). Thus, a ternary mixture of AF647, mcMMAF, and NEM could be prepared in an appropriate ratio to achieve any desired level of AF647 and mcMMAF loading (provided that the sum of the two is no greater than 10 for a murine IgG1 or IgG2a). To determine the correct mixture of these three reagents necessary to achieve a desired loading level, their relative reactivities were determined. This was done by preparing 1:1 mixtures of mcMMAF:NEM and AF647:NEM and reacting these mixtures with a fully reduced murine IgG1 immobilized on Protein G. The level of fluorophore loading in the resulting AF647 conjugate was determined from its 650 nm/280 nm absorbance ratio by reference to FIG. 5, while the mcMMAF loading in the resulting drug conjugate was determined by PLRP chromatography. These data are shown in the table below; the mole fraction on antibody is the loading of each reagent (AF647 or mcMMAF) divided by 10, the total number of maleimides which conjugate to the reduced murine IgG1; the NEM mole fraction is 1 minus the reagent mole fraction; and the relative reactivity is the ratio of the reagent mole fraction to the NEM mole fraction. In this analysis, NEM is assigned a relative reactivity value of 1.

| 1:1 mix | Loading | Mole fraction on antibody | NEM mole fraction on antibody | Relative Reactivity |
| --- | --- | --- | --- | --- |
| AF647:NEM | 2.88 | 0.288 | 0.712 | 0.404 |
| mcMMAF:NEM | 3.75 | 0.375 | 0.625 | 0.6 |

To convert these relative reactivity values into an appropriate ratio of maleimides to use in the ternary mixture, it is first necessary to define the desired loading levels of each reagent on the final conjugated antibody. For this example, a target loading of 4.5 mcMMAF, 3 AF647, and 2.5 NEM will be used, again assuming that the antibody conjugate will have 10 available thiols when reduced. This corresponds to a conjugated mole fraction of 0.45, 0.3, and 0.25, respectively. The necessary calculations are then summarized in the table below.

| Reagent | Conjugated Mole Fraction Target | Relative Reactivity (see table above) | Mole Fraction RelativeReactivity | required mole fraction in maleimide mix |
| --- | --- | --- | --- | --- |
| mcMMAF | 0.45 | 0.6 | 0.75 | 0.43 |
| AF647 | 0.3 | 0.404 | 0.74 | 0.43 |
| NEM | 0.25 | 1 | 0.25 | 0.14 |

Briefly, the target value for the conjugated mole fraction of each reagent is divided by its relative reactivity factor which was determined above using 1:1 mixes of the different reagents. This value is then converted to a required mole fraction in the maleimide mixture by dividing the value by the sum of the values for all reagents. For example, for mcMMAF, 0.45/0.6=0.75; 0.75/(0.75+0.74+0.25)=0.43. In this manner, a mixture of mcMMAF, AF647, and NEM in a ratio of 0.43:0.43:0.14 would be predicted to yield antibody conjugates with an average loading 4.5, 3, and 2.5 for the three reagents, respectively. In like manner, different ratios of the reagents could be calculated to achieve different loading levels on the conjugate, or ratios for other reagents could be calculated once their relative reactivities had been determined.

Example 5

Demonstration of the Consistency of Drug Loading Across Samples

Figure 6:
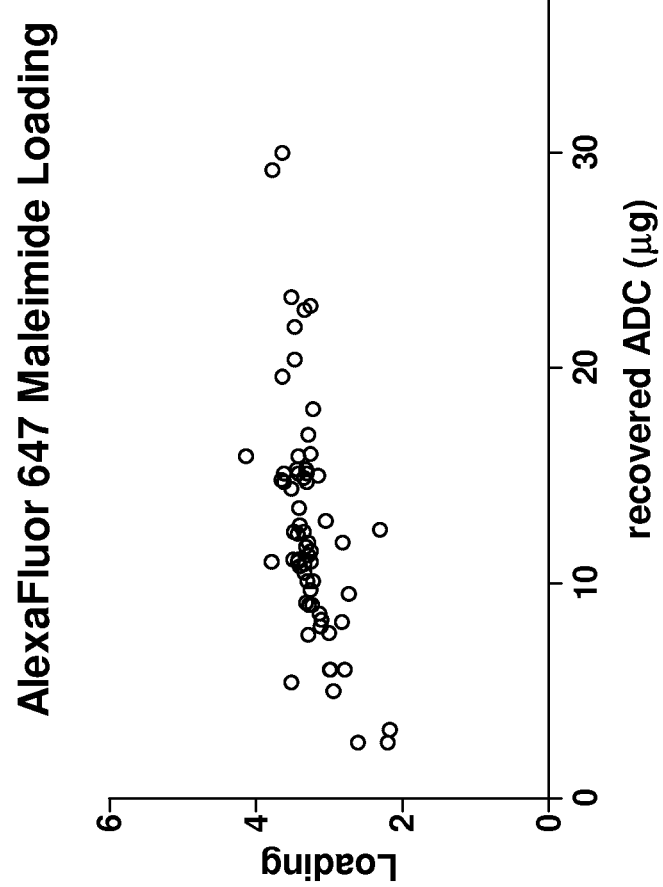
FIG. 6. This figure demonstrates the consistency of Alexa Fluor® 647 loading across 65 samples. The fluorophore loading was determined by obtaining the 650 nm/280 nm absorbance ratio of each antibody conjugate sample and referring back to FIG. 5 to determine the fluorophore loading associated with the absorbance ratio.
Figure 7:
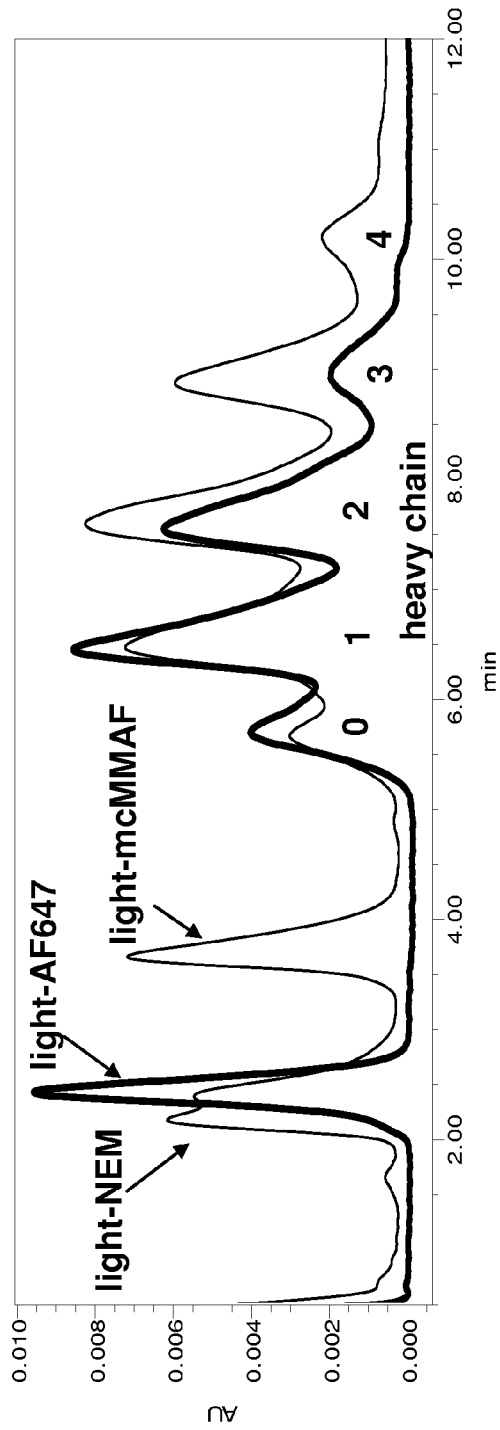
FIG. 7. This figure provides a PLRP chromatogram of an mcMMAF-AF647-NEM mixed conjugate. The antibody has 5 reducible disulfides. This figure provides an overlay of two analytical wavelengths. The 280 nm wavelength represented by a light solid line detects all of the peaks containing protein and the 620 nm wavelength represented by a heavy solid line detects all of the peaks containing at least one Alexa Fluor® 647.
Figure 8:
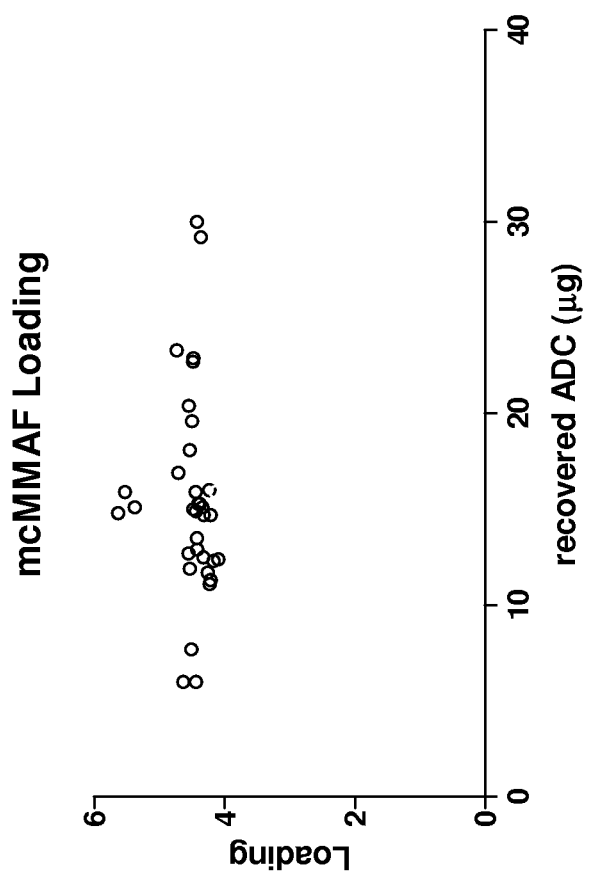
FIG. 8. This figure illustrates the consistency of mcMMAF loading across 34 samples.
Figure 9:
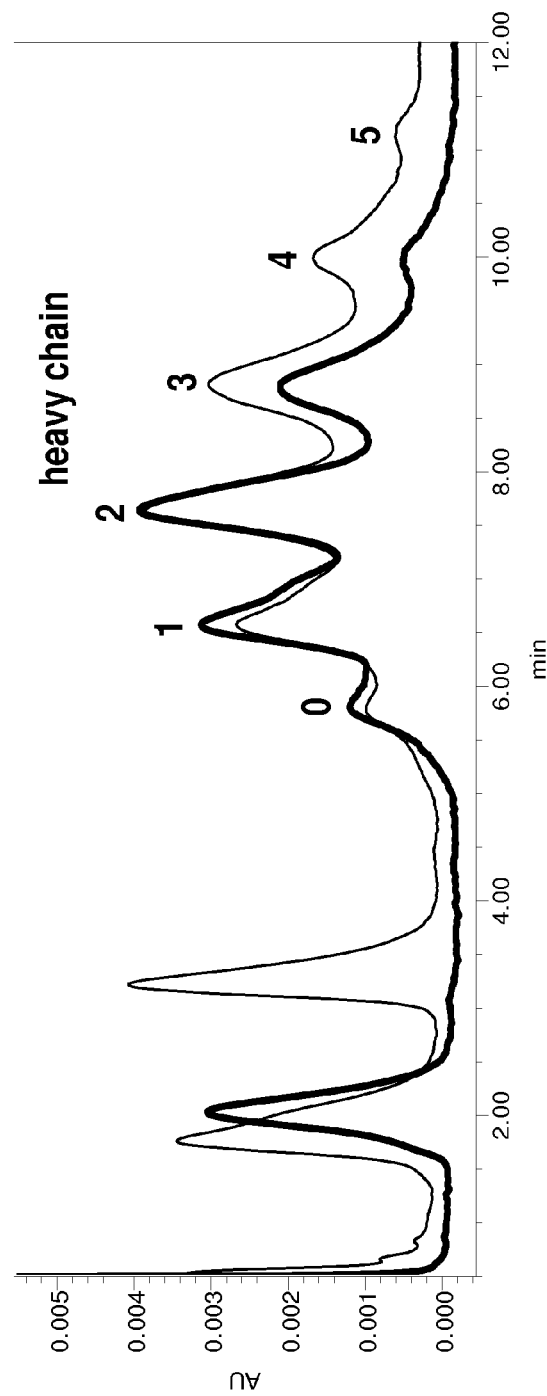
FIG. 9. This figure provides a PLRP chromatogram of an mcMMAF-AF647-NEM mixed conjugate. The antibody has 6 reducible disulfides (e.g., a murine IgG2b). The 280 nm wavelength is represented by a light solid line and the 620 nm wavelength is represented by a heavy solid line.
Figure 10:
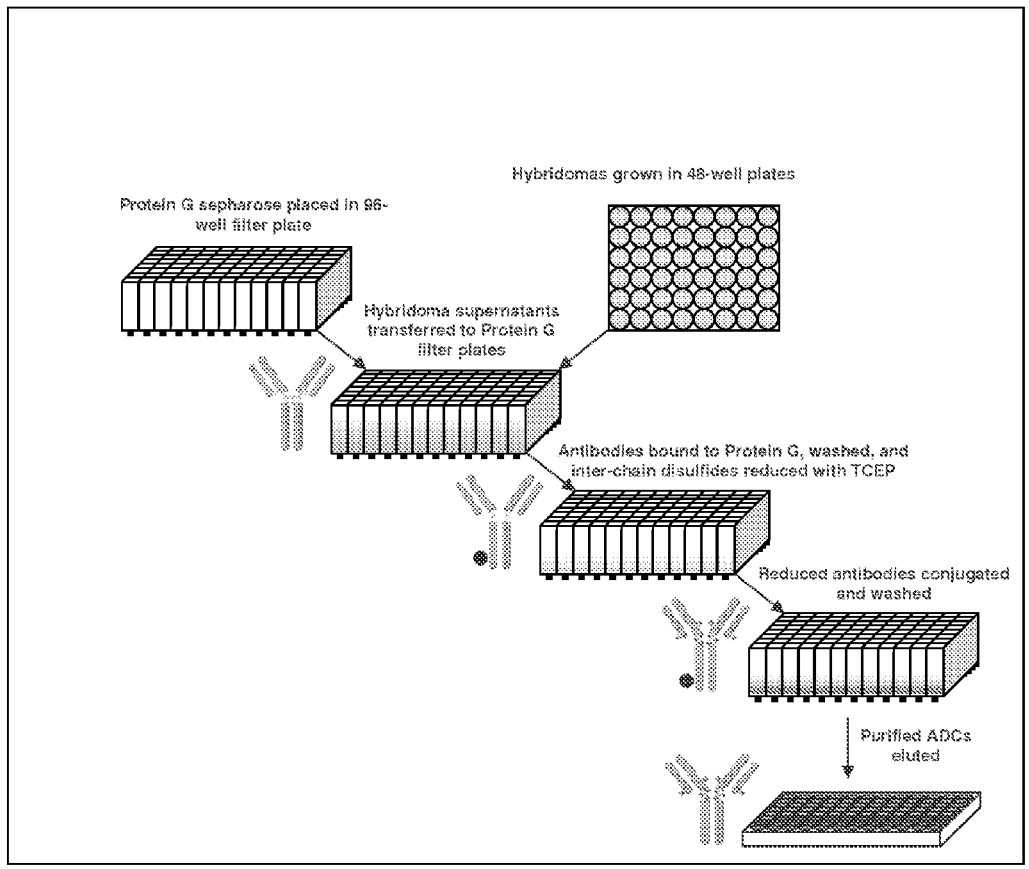
FIG. 10. This figure provides an exemplary scheme for plate-based solid phase synthesis of ADCs.
Figure 11:
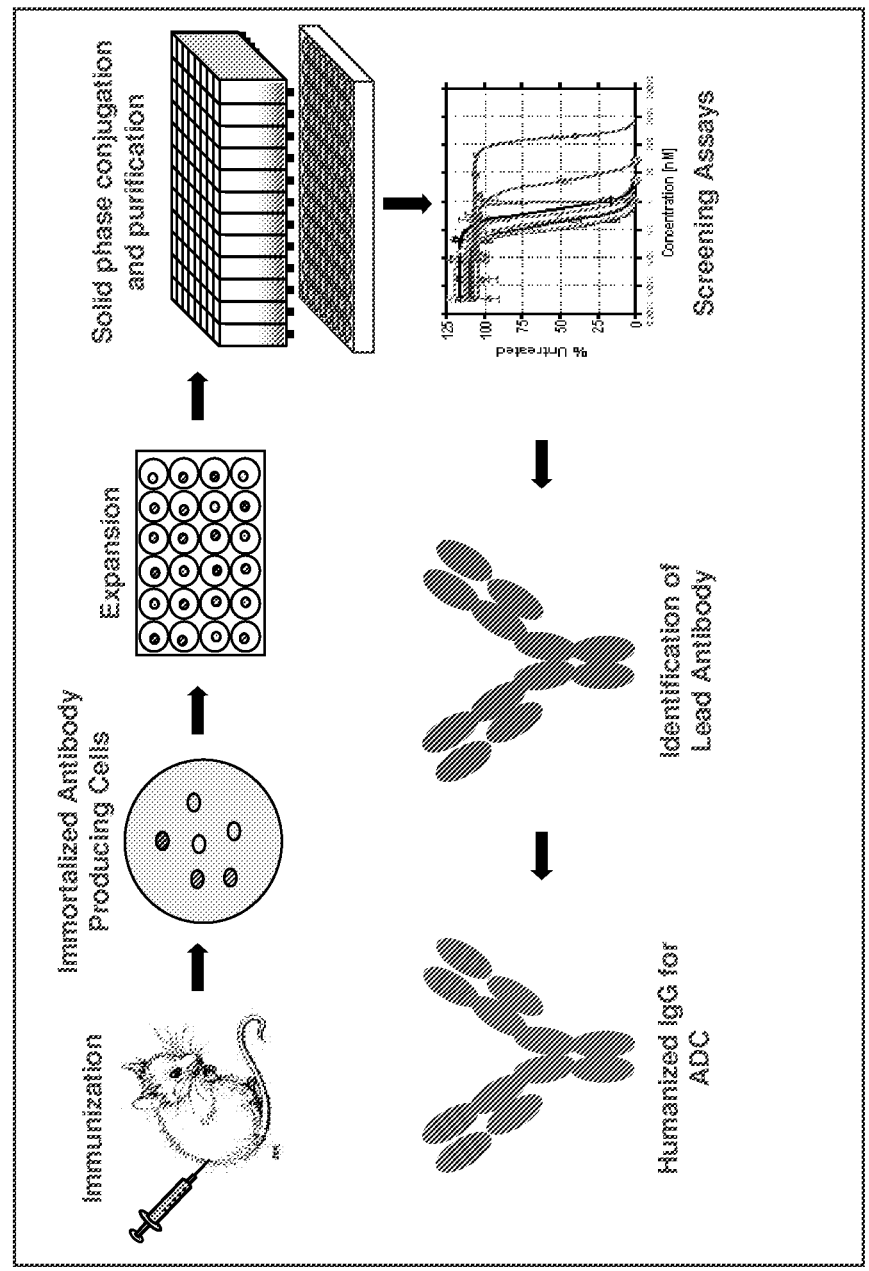
FIG. 11. This figure provides an exemplary scheme for application of solid phase conjugation technology to the discovery of ADCs with desirable properties.

A solution of mcMMAF, AF647 maleimide, and NEM was prepared in a ratio of 0.43:0.43:0.14 and used to conjugate a panel of antibodies by the present methods. These antibodies had been generated from 1.5 mL of bovine IgG-depleted hybridoma culture media, using newly fused hybridomas resulting from a murine immunization campaign. One 96-well plate of samples was subjected to analysis to determine the drug and fluorophore loading consistency of the resulting mixed conjugates. The fluorophore loading was determined by the 650 nm/280 nm absorbance ratio of each sample, measured in an absorbance plate reader, by reference to the linear relationship shown in FIG. 5. The resulting data are shown in FIG. 6, plotted against the quantity of conjugate that each sample yielded; the data are shown only for those samples which yielded at least 2.5 µg of conjugate, as lower quantities than this did not produce 280 nm absorbance values significantly above the baseline. There were 65 samples on the plate which met this 2.5 µg threshold and are plotted in FIG. 6. As can be seen in the figure, the loading is scattered between 2 and 4 fluorophores per antibody, with a calculated mean of 3.26 and a coefficient of variation of 10.2%. The mean loading of 3.26 differs by less than 10% from the targeted loading of 3. Importantly, the range of observed fluorophore loading levels fell within the region of the fluorescence vs loading curve (FIG. 4) where the fluorescence does not change greatly, due to the self-quenching phenomenon. In other words, the difference in observed fluorescence between antibodies with 2, 3, or 4 fluorophores per antibody is expected to be less than 20%. The mcMMAF loading was determined by PLRP chromatography; a sample PLRP chromatogram of an mcMMAF-AF647-NEM antibody conjugate is shown in FIG. 7. This figure is an overlay of two analytical wavelengths, 280 nm to detect all of the peaks containing protein, and 620 nm to detect those peaks containing at least one Alexa Fluor® 647. As can be seen in this figure, the light chain with NEM (2.2 minutes) is slightly resolved from the light chain with Alexa Fluor® 647 (2.5 minutes), but both are well resolved from the light chain with mcMMAF (3.8 minutes), illustrating that the PLRP column separates species well on the basis of mcMMAF loading but not AF647 loading. Since the light chain contains only one cysteine which is reduced by the TCEP treatment, these are the only light chain species present, and the NEM and mcMMAF peaks do not have absorbance at 620 nm as they contain no AF647. The heavy chain peak cluster is more complicated due to the fact that with 4 available thiols, each peak is not a single species. For example, the peak corresponding to heavy chain with 2 copies of mcMMAF (7.7 minutes) is a collection of heavy chain species which also contain 2 AF647, 2 NEM, or 1 AF647 and 1 NEM; these various species are not separated by the PLRP column. This feature of the separation permits these data to be used to assess strictly the mcMMAF loading without being affected by the presence of AF647 or NEM. Using this method, the mcMMAF loading levels were determined for 34 samples from the plate of hybridoma supernatants, and are plotted in FIG. 8 against the quantity of conjugate that each sample yielded. As can be seen in the figure, the loading is scattered between 4 and 6 copies of mcMMAF per antibody, with a calculated mean of 4.51 and a coefficient of variation of 7.75%. The mean loading of 4.51 is exactly at the targeted level of 4.5. As can be seen in the figure, there are 3 outliers with loading levels greater than 5; the PLRP chromatograms from these samples contain a heavy chain species with 5 copies of mcMMAF, indicating the presence of an additional reducible disulfide on the heavy chain of these antibodies (see FIG. 9 as an example), suggesting that these antibodies are of the murine IgG2b isotype. Thus, the higher loading observed in these samples is not due to disproportionate loading of mcMMAF compared to the other antibodies, but rather that these antibodies have 20% more available thiols (12 rather than 10) and therefore would be expected to be loaded with each reagent at levels 20% higher. If these three are excluded from the analysis and only those antibodies with 10 available thiols are considered, the mean mcMMAF loading for the 31 antibodies is 4.42 and the coefficient of variation falls to 3.45%. These results illustrate the consistency of reagent loading (mcMMAF and AF647) achieved by the present method across a panel of antibodies of variable isotype and in variable quantities from a panel of newly fused hybridomas.

Example 6

Exemplary Method for Making Antibody Conjugates Loaded with Drug-Linker and Capping Agent Hybridoma supernatants were prepared as 4.5 mL solutions in 5 mL round-bottom tubes. 150 uL Protein G resin slurry MILLIPORE™PROSEP-G™) was added to each. Tubes were capped and rotated overnight at 5° C. Two control tubes were also prepared, one with bovine IgG-depleted growth media (to serve as a blank) and one with this same media spiked with 100 ug of a control antibody. On the following morning, resin was transferred from tubes to a 2 mL, 96-well filter plate with a 2.5 um polypropylene frit (Seahorse Bioscience) using a 1250 uL MATRIX-™pipettor. The supernatant in the filter plate was pulled through by brief application of vacuum. After all wells had dried (<30 seconds), the plate was centrifuged at 500× g for 3 minutes to ensure complete pulldown of all fluids and resin. After spinning, the filter plate was replaced on the manifold and each well received 500uL PBS. The plate was then shaken at 1200 RPM on the Thermomixer for 30 seconds to slurry the resin. The PBS was then pulled through by vacuum. This process was repeated twice, for a total of 3 PBS washes. This process was then repeated with 3× gPBS, and then followed by a another wash with PBS. Following this final wash, the plate was spun as before.

The bound antibodies were then reduced by adding 500 uL of 20 mM TCEP in 250 mM $KPO_4$, 150 mM NaCl, pH 7, 1 mM EDTA and shaking for 2 hours at 37° C. on the Thermomixer. Following reduction, the TCEP solution was pulled through by vacuum and then spun as above, then washed with PBS+1 mM EDTA as described above. This was repeated 4×, for a total of 5 washes.

The bound antibodies were then conjugated to a mixture of NEM and mc-MMAF in a molar ratio of 4:6. A stock of NEM+mc-MMAF at a total maleimide concentration of 12 mM was prepared in advance. 1.1 mL of this solution was added to 55 mL of 10% DMSO, transferred to a multichannel reservoir, and 500 uL added to each well of the filter plate, which was then shaken for 30 minutes at 22° C. Following conjugation, the maleimide solution was pulled through by vacuum and then spun as above. The centrifuge speed was increased to 1500× g to complete the drying. Wells were then washed twice with 500 uL of 10% DMSO in PBS, then three times with PBS.

The bound ADCs were then eluted by adding 200 uL of 100 mM glycine, pH 2.0 to each well and shaking for 3 minutes at 1200 RPM, 22° C. on the Thermomixer. While shaking, 20 uL of neutralization buffer (1M dibasic phosphate+0.1% Tween-20) was added to each well of a 350 uL collection plate. When 3 minutes had elapsed, the ADCs were eluted into the collection plate by spinning at 1500× g for 6 minutes.

200 uL of each ADC solution were transferred to a Costar UV assay plate. A second plate was prepared with neutralized elution buffer to serve as a blank. A280 measurements were carried out with a Molecular Devices SpectraMax plate reader to determine protein concentrations.

Finally, ADCs were sterile filtered. In the BSC, a sterile 0.2 um filter plate (Millipore) was fastened to a sterile 1 mL collection plate (Matrix) using lab tape. The ADC solutions were then added to the filter plate and spun at 500× g for 3 minutes. The assembly was then transferred to the BSC and disassembled, then the collection plate capped with a sterile cap mat (Matrix).

Example 7

Exemplary Method for Making Antibody Conjugates Loaded with Drug-Linker, Capping Agent, and Fluorophore Newly fused hybridomas were plated in methylcellulose media (GENETIX™) containing HAT and fluorescently labeled anti-mouse IgG (GENETIX™). Clonal, IgG-producing colonies were selected and deposited into a 96W plate containing HSFM (INVITROGEN™) plus IgG-depleted cloning factor (Roche). Four-fold dilutions of unpurified hybridoma culture supernatants were incubated with target tumor cells in a homogenous assay containing 100 ng/ml of Cy5-labeled anti-mouse secondary antibody (Jackson Labs). Hybridoma binding to the tumor cells was detected using an FMAT8200 (APPLIED BIOSYSTEMS™) and positive wells were expanded into 48W dishes containing 2 mls of HSFM ( INVITROGEN™) plus IgG-depleted cloning factor. Antibodies from 48W extinguished supernatants were used for solid-phase purification and conjugation Hybridoma supernatants (1.5 mL) were transferred to 96-well deep well plates with a 0.45 um polypropylene frit (Seahorse Bioscience). To enable quantitation of conjugate concentration by fluorescence, a standard murine antibody was included in the conjugation. 50 ug of the standard antibody was placed in 4 wells of the plate with blank media (200 ug total). Additionally, 3 wells contained only blank media for determination of background fluorescence.

100 uL of PBS was placed in each well of a 96-well deep well filter plate fitted with a 2.5 um polypropylene filter (Seahorse Bioscience). 20 uL Protein G resin slurry (GE Life Sciences GAMMABIND PLUS™) was added to each well.

The filter plate containing the Protein G resin was placed as the receiver plate in a vacuum manifold, and the manifold assembled. The 0.45 um filter plate containing the antibody samples and standards was placed on top of the manifold, and the supernatants transferred to it. By application of vacuum, supernatants were then filtered through the 0.45 um filters into the plate containing the Protein G resin. The resin plate was then shaken for 2 hours at room temperature at 1200 RPM using an Eppendorf Thermomixer to effect binding to the Protein G. The residual supernatant was then filtered into a 2 mL deep well receiver plate by centrifugation at 500× g for 5 minutes.

A solution of 10 mM tricarboxyethyl phosphine (TCEP) in 100 mM potassium phosphate, pH 7.4, 150 mM NaCl, was added to the plate (150 uL per well). The plate was then shaken as above for 30 minutes, then removed from the shaker and centrifuged for 2 minutes at 500× g. The resin was washed four times with 500 uL of PBS containing 1 mM EDTA, with vacuum filtration following each wash. Following the final wash, another 500 uL PBS/EDTA added and removed by centrifugation for 3 minutes at 500× g.

Individual stocks of drug-linker (mcMMAF), Alexa Fluor® 647, and NEM were prepared at 10 mM in DMSO. These stocks were then blended into a single solution at the following ratio for conjugation:

3:3:1 mcMMAF:Alexa Fluor® 647:NEM 140 uL of this solution was dissolved in 15 mL of PBS/EDTA, and 150 uL added to each well of the washed plate. The plate was then shaken as above for 15 minutes, then removed from the shaker and centrifuged for 2 minutes at 500× g. The resin was washed four times with 500 uL of PBS, with vacuum filtration following each wash. Following the final wash, another 500 uL of PBS was added and removed by centrifugation for 3 minutes at 500× g.

10 uL of 1M potassium phosphate pH 7.4 was added to each well of a 350 uL 96-well clear-bottom assay plate. The resin plate was placed atop the assay plate and 100 uL elution buffer (50 mM glycine pH 2.5+0.08% Tween-20) added to each well. The plate was gently agitated by manual rocking for 2 minutes, then centrifuged for 2 minutes at 500× g to collect the eluted antibody conjugates in the assay plate. The assay plate was immediately placed in a fluorescence plate reader (Molecular Devices) and shaken for 10 seconds using the plate reader shaker to ensure complete mixing of the neutralization buffer into the elution buffer. The fluorescence of each well at 675 nm was then measured using an excitation of 635 nm with a 665 nm cutoff filter. The solutions in the wells containing the standards were removed and pooled into a single standard solution, and the concentration of this standard was determined by a conventional A280 absorbance method in a 1 cm cuvet. A dilution series of this standard was then prepared (using neutralized elution buffer as the diluent) down to a concentration of 1 ug/mL. 110 uL of each standard was then transferred to a clean 350 uL clear bottom assay plate and the fluorescence again measured on the plate reader. A second-order polynomial curve was fit to the fluorescence values of the standards, and the concentrations of the samples were assigned by interpolation to this standard curve.

Finally, ADCs were sterile filtered. In the BSC, a sterile 0.2 um filter plate (MILLIPORE™) was fastened to a sterile 1 mL collection plate (MATRIX™) using lab tape. The ADC solutions were then added to the filter plate and spun at 500× g for 3 minutes. The assembly was then transferred to the BSC and disassembled, then the collection plate capped with a sterile cap mat (MATRIX™).

Mixed antibody conjugates containing fluorophore and drug were tested in cell binding and cytotoxicity assays. For cell-based binding assays, the antibody panel was diluted at 1:200 and 1:1000 in PBS+2% serum and incubated on target cells for 2 hours at room temperature in 96W black plates. A control antibody was used on each plate to generate a saturation binding curve for human and cyno forms of the antigen. Plates were then analyzed in an FMAT8200 and mean fluorescence intensity values for each dilution were plotted on the saturation binding curve to estimate test antibody affinity on human and cyno forms of the antigen. Hybridomas that showed equivalent binding to human and cyno antigen were advanced for cytotoxicity studies. Cytoxicity studies were done by plating 5,000 cells per well in the appropriate growth media. Mixed conjugates were added to a final dilution of 1:100 and 1:1000, respectively. Tumor cells were incubated with drug/fluorophore conjugates for 96 hours at 37° C. Cell Titer Glo (Promega) was used to measure cell viability and the potency of drug/fluorophore conjugates was assessed based on the percent viability relative to untreated control cells. Drug/fluorophore conjugates that resulted in <70% viability of tumor cells at 1 nM concentrations were advanced for further testing.

Example 8

IgG Depletion

Cloning Factor is commonly used as a media component in expanding hybridoma cell lines after fusion with murine B cells. Cloning Factor contains important cell mediators that where harvested from the supernatant of healthy thriving cells and these help the new hybridoma fusions recover and begin to grow more robustly. It is suspected that the harvested supernatant from the healthy thriving cells that makes up the cloning factor contains bovine serum as a media component which would include bovine albumin, IgG and other serum proteins. It is the bovine IgG that is of concern in this case because even a small amount of contaminating IgG can affect the quantitative recovery of the antibodies and quantitation of the resulting ADCs.

The method for removing bovine IgG from Cloning Factor is as follows. 5 ml Protein G column is equilibrated with 1× gPBS (5 Column Volumes, CV), 25 ml. Contents of the Hybridoma Cloning factor are loaded into a 60 cc syringe. A syringe is attached to the Protein G column and connected to a syringe pump. The pump is set to 3 ml/min, the Cloning Factor is passed over the Protein G column and the effluent is collected. The effluent contains the IgG depleted Cloning factor. Bovine IgG will bind to the Protein G column The IgG depleted Hybridoma Cloning factor is sterile filtered in a biosafety cabinet using a 0.22 µm syringe filter.

What is claimed:

1. A method for making antibody conjugates for use in high throughput screening assays comprising the steps of:
providing a plurality of antibody-containing samples that vary with respect to antibody quantity and antibody sequence provided that, in a majority of the antibody-containing samples, substantially all of the antibody present in each of the samples is of the same sequence;
immobilizing the antibodies of the antibody-containing samples on a solid support to provide a plurality of antibody-containing samples comprising immobilized antibodies;
fully reducing the reducible disulfide bonds of the immobilized antibodies to provide a plurality of samples comprising reduced immobilized antibodies; wherein the reduction is selective for reducible disulfide bonds;
reacting the reduced immobilized antibodies with capping agent, drug or drug-linker, and optionally a detection agent to provide immobilized antibody conjugates; wherein the capping agent, drug or drug-linker, and optional detection agent selectively react with reactive thiols, the capping agent, drug or drug-linker, and optional detection agent are provided in molar excess, and the ratio of capping agent, drug or drug linker, and optional detection agent is selected so as to achieve a desired level of drug loading; and
eluting the immobilized antibody conjugates to provide a plurality of antibody conjugate samples.

2. The method of claim 1 wherein the reducible disulfide bonds are naturally occurring.

3. The method of claim 1 wherein the antibodies have substantially the same number of reducible disulfide bonds.

4. The method of claim 1 wherein the quantity of antibody present in the antibody-containing samples prior to immobilizing, reduction, conjugation, and elution is not known.

5. The method claim 1 wherein the antibody-containing samples have from 1 µg to 100 µg of antibody present in the sample.

6. The method of claim 1 wherein the antibody containing samples have from 1 µg to 20 µg of antibody present in the sample.

7. The method claim 1 wherein the capping agent, drug or drug-linker and detection agent comprise a maleimide group.

8. The method of claim 1 wherein the drug-linker loading between samples is substantially uniform.

9. The method of claim 1 wherein the antibody conjugate samples have an average drug-linker loading of about 4 drug-linkers per antibody.

10. The method of claim 1 wherein the antibody-containing samples are unpurified CHO cell culture supernatant.

11. The method of claim 1 wherein the antibody-containing samples are cell culture supernatant samples and_substantially all of the cell culture media used for antibody production was IgG depleted media.

12. The method of claim 1 further comprising the step of:
assaying for an activity of the antibody conjugates and making a comparison between the antibodies that constitute the antibody conjugates based on an activity of the antibody conjugates.

13. The method claim 12 wherein the activity is cytotoxicity.

14. The method of claim 1 wherein the antibody-containing samples are unpurified hybridoma supernatant samples comprising unquantified antibody produced from hybridoma clones and wherein substantially all of the antibody present in each sample is from a single hybridoma clone.

15. The method of claim 14 wherein substantially all of the cell culture media used for antibody production was IgG depleted media.

16. The method of claim 14 wherein there is from 1 µg to 100 µg of antibody present in each sample of hybridoma supernatant.

17. The method of claim 14 wherein there is from 1 µg to 50 µg of antibody present in each sample of hybridoma supernatant.

18. The method of claim 14 further comprising the steps of (i) determining the actual or relative quantity of antibody present in the antibody conjugate samples; (ii) assaying an activity of the antibody conjugates; (iii) selecting an antibody based on the results of the assay and the actual or relative quantity of antibody present in the antibody conjugate samples.

19. The method of claim 14 wherein the detection agent is a fluorescent label.

20. The method of claim 14 wherein the capping agent, drug or drug-linker and detection agent comprise a maleimide group.

21. The method of claim 1 further comprising the steps of:
performing a cytotoxicity assay on the_antibody conjugates; and selecting an antibody of the basis of the outcome of the assay.

22. A method for making antibody conjugates for use in antibody screening assays comprising the steps of:
providing a plurality of antibody containing samples that vary with respect to antibody quantity and antibody sequence provided that, in a majority of the plurality of the antibody containing samples, substantially all of the antibody present in each of the samples is of the same sequence;
immobilizing the antibodies of the antibody containing samples_on a solid support to provide a plurality of samples comprising immobilized antibodies;
fully reducing the reducible disulfide bonds of the immobilized antibodies to provide a plurality of samples comprising reduced immobilized antibodies, wherein the reduction is selective for reducible disulfide bonds;
reacting the reduced immobilized antibodies with capping agent, and a detection agent to provide a plurality of samples comprising immobilized antibody conjugates, wherein the capping and detection agent selectively react with reactive thiols, the capping agent, and detection agent are provided in molar excess, and the ratio of capping agent and detection agent is selected so as to achieve a desired level of capping agent and/or detection agent loading; and
eluting the antibody conjugates to provide a plurality of antibody conjugate samples comprising free antibody conjugates.

23. The method of claim 22 further comprising the steps of:
performing a cytotoxicity assay on the antibody conjugates; and selecting an antibody of the basis of the outcome of the assay.

* * * * *